United States Patent
Faries, Jr. et al.

(10) Patent No.: US 7,854,230 B2
(45) Date of Patent: Dec. 21, 2010

(54) HEATED MEDICAL INSTRUMENT STAND WITH SURGICAL DRAPE AND METHOD OF DETECTING FLUID AND LEAKS IN THE STAND TRAY

(75) Inventors: Durward I. Faries, Jr., Las Vegas, NV (US); Bruce R. Heymann, Vienna, VA (US); David Hendrix, Ashburn, VA (US)

(73) Assignee: O.R. Solutions, Inc., Chantilly, VA (US)

( * ) Notice: Subject to any disclaimer, the term of this patent is extended or adjusted under 35 U.S.C. 154(b) by 1968 days.

(21) Appl. No.: 10/836,237

(22) Filed: May 3, 2004

(65) Prior Publication Data

US 2004/0208780 A1 Oct. 21, 2004

Related U.S. Application Data

(63) Continuation-in-part of application No. 10/372,674, filed on Feb. 25, 2003, now Pat. No. 6,910,485, which is a continuation-in-part of application No. 09/983,021, filed on Oct. 22, 2001, now Pat. No. 6,810,881, application No. 10/836,237, filed on May 3, 2004.

(60) Provisional application No. 60/467,127, filed on May 2, 2003.

(51) Int. Cl.
*A61F 5/37* (2006.01)
*A61F 13/00* (2006.01)
*A61B 19/08* (2006.01)
*A47K 3/02* (2006.01)
*A47K 1/06* (2006.01)
*H05B 1/00* (2006.01)
*H05B 3/00* (2006.01)
*H05B 11/00* (2006.01)
*H05B 1/02* (2006.01)
*D06F 75/26* (2006.01)
*F24C 1/00* (2006.01)
*F24C 11/00* (2006.01)

(52) U.S. Cl. .................. 128/849; 128/846; 128/850; 128/852; 4/580; 4/655; 219/218; 219/221; 219/246; 219/248; 219/494; 392/308

(58) Field of Classification Search ......... 128/849–856; 62/66, 68, 340, 342; 4/580, 655, 658; 219/212, 219/217, 494; 392/308
See application file for complete search history.

(56) References Cited

U.S. PATENT DOCUMENTS

| | | |
|---|---|---|
| 2,599,192 A | 6/1952 | Miller |
| 2,613,511 A | 10/1952 | Walsh |
| 2,807,701 A | 9/1957 | Conlin et al. |
| 3,807,954 A | 4/1974 | McDonald |
| 3,869,596 A | 3/1975 | Howie |
| 3,902,484 A | 9/1975 | Winters |
| 4,053,954 A | 10/1977 | Chapman |
| 4,270,067 A | 5/1981 | Thomas et al. |
| 4,284,880 A | 8/1981 | Keiser |
| 4,393,659 A | 7/1983 | Keyes et al. |
| 4,458,139 A | 7/1984 | McClean |
| 4,474,016 A | 10/1984 | Winchell |
| 4,522,041 A | 6/1985 | Menzel |
| 4,625,098 A | 11/1986 | Joe |
| 4,782,835 A | 11/1988 | Bernardini |
| 4,828,876 A | 5/1989 | Ohhara et al. |
| 4,869,271 A | 9/1989 | Idris |
| 4,903,710 A | 2/1990 | Jessamine et al. |
| 4,934,152 A | 6/1990 | Templeton |
| 4,967,061 A | 10/1990 | Weber, Jr. et al. |
| 5,040,699 A | 8/1991 | Gangemi |
| 5,042,455 A | 8/1991 | Yue et al. |
| 5,042,981 A | 8/1991 | Gross |
| 5,129,033 A | 7/1992 | Ferrara et al. |
| 5,163,299 A | 11/1992 | Faries, Jr. et al. |
| 5,174,306 A | 12/1992 | Marshall |
| 5,310,524 A | 5/1994 | Campbell et al. |
| 5,331,820 A | 7/1994 | Faries, Jr. et al. |
| 5,333,326 A | 8/1994 | Faries, Jr. et al. |
| 5,345,063 A | 9/1994 | Reusche et al. |
| 5,351,675 A | 10/1994 | Brodsky |
| 5,363,746 A | 11/1994 | Gordon |
| 5,374,813 A | 12/1994 | Shipp |
| 5,379,703 A | 1/1995 | Marshall |

| | | |
|---|---|---|
| 5,383,476 A | 1/1995 | Peimer et al. |
| 5,386,835 A | 2/1995 | Elphick et al. |
| 5,396,905 A | 3/1995 | Newman et al. |
| 5,400,267 A | 3/1995 | Denen et al. |
| 5,400,616 A | 3/1995 | Faries, Jr. et al. |
| 5,402,644 A | 4/1995 | Faries, Jr. et al. |
| 5,429,801 A | 7/1995 | Faries, Jr. et al. |
| 5,435,322 A | 7/1995 | Marshall |
| 5,443,082 A | 8/1995 | Mewburn |
| 5,449,892 A | 9/1995 | Yamada |
| 5,457,962 A | 10/1995 | Faries, Jr. et al. |
| 5,463,213 A | 10/1995 | Honda |
| 5,480,302 A | 1/1996 | Fife |
| 5,502,980 A | 4/1996 | Faries, Jr. et al. |
| 5,517,170 A | 5/1996 | Peters et al. |
| 5,522,095 A | 6/1996 | Faries, Jr. et al. |
| 5,522,805 A | 6/1996 | Vancaillie et al. |
| 5,524,478 A | 6/1996 | Joy et al. |
| 5,524,643 A | 6/1996 | Faries, Jr. et al. |
| 5,531,697 A | 7/1996 | Olsen |
| 5,539,185 A | 7/1996 | Polster |
| 5,549,543 A | 8/1996 | Kim |
| 5,551,240 A | 9/1996 | Faries, Jr. et al. |
| 5,615,423 A | 4/1997 | Faries, Jr. et al. |
| 5,653,938 A | 8/1997 | Faries, Jr. et al. |
| 5,658,478 A | 8/1997 | Roeschel et al. |
| 5,664,582 A | 9/1997 | Szymaitiz |
| 5,715,547 A | 2/1998 | Becker et al. |
| 5,717,188 A | 2/1998 | Vaillancourt |
| 5,800,352 A | 9/1998 | Ferre et al. |
| 5,809,788 A | 9/1998 | Faries, Jr. et al. |
| 5,816,252 A | 10/1998 | Faries, Jr. et al. |
| 5,857,467 A | 1/1999 | Faries, Jr. et al. |
| 5,862,672 A | 1/1999 | Faries, Jr. et al. |
| 5,879,621 A | 3/1999 | Faries, Jr. et al. |
| 5,950,438 A | 9/1999 | Faries, Jr. et al. |
| 6,003,328 A | 12/1999 | Faries, Jr. et al. |
| 6,035,855 A | 3/2000 | Faries, Jr. et al. |
| 6,087,636 A | 7/2000 | Faries, Jr. et al. |
| 6,091,058 A | 7/2000 | Faries, Jr. et al. |
| 6,102,044 A | 8/2000 | Naidyhorski |
| 6,255,627 B1 | 7/2001 | Faries, Jr. et al. |
| 6,259,067 B1 | 7/2001 | Faries, Jr. et al. |
| 6,341,704 B1 | 1/2002 | Michel, Jr. |
| 6,371,121 B1 | 4/2002 | Faries, Jr. et al. |
| 6,448,571 B1 * | 9/2002 | Goldstein ............... 250/515.1 |
| 6,524,742 B1 | 2/2003 | Emanuel et al. |
| 6,586,950 B1 | 7/2003 | Sargent et al. |
| 6,593,552 B1 | 7/2003 | Li |
| 6,701,174 B1 * | 3/2004 | Krause et al. ............... 600/407 |
| 6,810,881 B2 | 11/2004 | Faries, Jr. et al. |
| 6,860,271 B2 | 3/2005 | Faries, Jr. et al. |
| 6,884,970 B2 * | 4/2005 | Lehman .................. 219/432 |
| 6,910,485 B2 | 6/2005 | Faries, Jr. et al. |
| 6,918,395 B2 | 7/2005 | Faries, Jr. et al. |
| 6,927,365 B2 | 8/2005 | Li |
| 7,041,941 B2 | 5/2006 | Faries, Jr. et al. |
| 7,176,030 B2 | 2/2007 | Faries, Jr. et al. |
| 7,276,675 B2 | 10/2007 | Faries, Jr. et al. |
| 7,307,245 B2 | 12/2007 | Faries, Jr. et al. |
| 7,309,472 B2 | 12/2007 | Michaelson et al. |
| 7,311,660 B2 | 12/2007 | Gomez |
| 7,347,210 B2 | 3/2008 | Faries, Jr. et al. |
| 7,350,373 B1 | 4/2008 | Faries, Jr. et al. |
| 7,417,205 B2 | 8/2008 | Faries, Jr. et al. |
| 7,418,966 B2 | 9/2008 | Faries, Jr. et al. |
| 7,671,302 B1 | 3/2010 | Faries, Jr. et al. |
| 7,728,262 B1 | 6/2010 | Faries, Jr. et al. |
| 2003/0132216 A1 | 7/2003 | Li |
| 2003/0231990 A1 | 12/2003 | Faries, Jr. et al. |
| 2004/0200480 A1 | 10/2004 | Faries, Jr. et al. |
| 2004/0200483 A1 | 10/2004 | Faries, Jr. et al. |
| 2004/0208780 A1 | 10/2004 | Faries, Jr. et al. |
| 2005/0247169 A1 | 11/2005 | Faries, Jr. et al. |
| 2006/0065276 A1 | 3/2006 | Kammer et al. |
| 2006/0086361 A1 | 4/2006 | Kammer et al. |
| 2006/0091128 A1 | 5/2006 | Kammer et al. |
| 2006/0091129 A1 | 5/2006 | Colonna |
| 2006/0194324 A1 | 8/2006 | Faries, Jr. et al. |
| 2006/0260443 A1 | 11/2006 | Faries, Jr. et al. |
| 2006/0289445 A1 | 12/2006 | Colonna |
| 2007/0089753 A1 | 4/2007 | Faries, Jr. et al. |
| 2009/0255540 A1 | 10/2009 | Faries, Jr. |
| 2010/0116811 A1 | 5/2010 | Liu et al. |
| 2010/0200561 A1 | 8/2010 | Faries, Jr. et al. |

FOREIGN PATENT DOCUMENTS

| | | |
|---|---|---|
| JP | 61-185967 | 11/1986 |
| JP | 06-123532 | 5/1994 |

OTHER PUBLICATIONS

Stainless Steel: Mayo Stands; Blickman's Manhattan Mayo Stand; retrieved from Internet Mar. 5, 2003; 1 page.

All-Tech Medical Resale Pre-Owned Physicians and Hospital Equipment; retrieved from Internet Mar. 5, 2003; 1 page.

"Electrically Conductive Polymer Film"; Creative Materials Incorporated; www.creativematerials.com; 1page.

"Electrically Conductive Polymer Nanocomposite Materials"; retrieved from Internet Apr. 24, 2003; www.afrlhorizons.com/Briefs/Sept02/ML0206.html; 2 pages.

Pique, A., et al.; "Processing of Functional Polymers and Organic Thin Films by the Matrix-Assisted Pulsed Laser Evaporation (MAPLE) Technique"; Applied Surface Science, vol. 186, 2002; pp. 408-415.

\* cited by examiner

*Primary Examiner*—Patricia M Bianco
*Assistant Examiner*—Brandon Jackson
(74) *Attorney, Agent, or Firm*—Edell, Shapiro & Finnan, LLC

(57) ABSTRACT

A medical instrument thermal treatment system according to the present invention is in the form of a stand including a thermally treated tray to thermally treat medical instruments. The stand includes a frame to support the tray, while a drape including a sensing device is disposed over the tray to form a drape container or receptacle within the tray for collecting a sterile medium. The tray is thermally treated to heat the sterile medium in order to warm medical instruments or other medical items placed in the tray. The sensing device provides a signal to the system indicating the presence of liquid and/or leaks within the drape container to facilitate control of system operation.

60 Claims, 8 Drawing Sheets

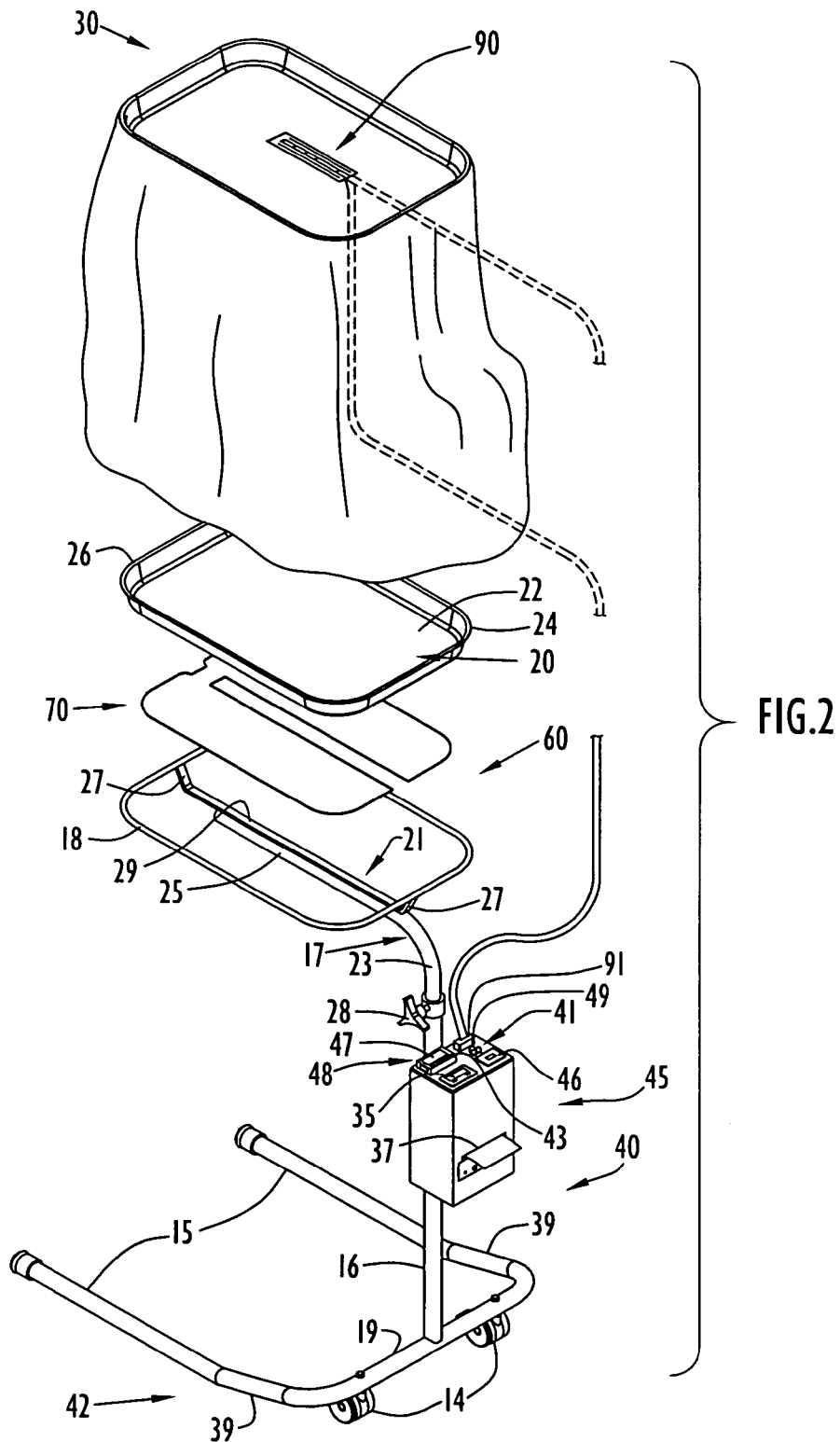

HEATED MEDICAL INSTRUMENT STAND WITH SURGICAL DRAPE AND METHOD OF DETECTING FLUID AND LEAKS IN THE STAND TRAY

CROSS-REFERENCE TO RELATED APPLICATIONS

This application is a continuation-in-part of U.S. patent application Ser. No. 10/372,674, now U.S. Pat. No. 6,910,485 entitled "Medical Solution Thermal Treatment System and Method of Controlling System Operation in Accordance with Detection of Solution and Leaks in Surgical Drape Containers" and filed Feb. 25, 2003, which is a continuation-in-part of U.S. patent application Ser. No. 09/983,021, now U.S. Pat. No. 6,810,881 entitled "Medical Solution Thermal Treatment System and Method of Controlling System Operation in Accordance with Detection of Solution and Leaks in Surgical Drape Containers" and filed Oct. 22, 2001. In addition, the present application claims priority from U.S. Provisional Patent Application Ser. No. 60/467,127, entitled "Heated Medical Instrument Stand With Surgical Drape and Method of Detecting Fluid and Leaks in the Stand Tray" and filed May 2, 2003. The disclosures of the aforementioned patent applications are incorporated herein by reference in their entireties.

BACKGROUND OF THE INVENTION

1. Technical Field

The present invention pertains to medical instrument stands, such as Mayo stands employed in operating rooms. In particular, the present invention pertains to a medical instrument stand for thermally treating a sterile surgical solution and medical instruments contained within a surgical drape container of a stand tray. In addition, the stand and drape detect the presence of solution and/or leaks within the drape container to control system operation. The stand is preferably utilized with surgical drapes employed for thermal treatment systems that thermally treat a sterile surgical liquid, such as the types disclosed in U.S. Pat. No. 4,934,152 (Templeton), U.S. Pat. No. 5,163,299 (Faries, Jr. et al.), U.S. Pat. No. 5,331,820 (Faries, Jr. et al.), U.S. Pat. No. 5,333,326 (Faries, Jr. et al.), U.S. Pat. No. 5,400,616 (Faries, Jr. et al.), U.S. Pat. No. 5,402,644 (Faries, Jr. et al.), U.S. Pat. No. 5,429,801 (Faries Jr. et al.), U.S. Pat. No. 5,457,962 (Faries, Jr. et al.), U.S. Pat. No. 5,502,980 (Faries, Jr. et al.), U.S. Pat. No. 5,522,095 (Faries, Jr. et al.), U.S. Pat. No. 5,524,643 (Faries, Jr. et al.), U.S. Pat. No. 5,551,240 (Faries, Jr. et al.), U.S. Pat. No. 5,615,423 (Faries, Jr. et al.), U.S. Pat. No. 5,653,938 (Faries, Jr. et al.), U.S. Pat. No. 5,809,788 (Faries, Jr. et al.), U.S. Pat. No. 5,816,252 (Faries, Jr. et al.), U.S. Pat. No. 5,857,467 (Faries, Jr. et al.), U.S. Pat. No. 5,862,672 (Faries, Jr. et al.), U.S. Pat. No. 5,879,621 (Faries, Jr. et al.), U.S. Pat. No. 5,950,438 (Faries, Jr. et al.), U.S. Pat. No. 6,003,328 (Faries, Jr. et al.), U.S. Pat. No. 6,035,855 (Faries, Jr. et al.), U.S. Pat. No. 6,087,636 (Faries, Jr. et al.), U.S. Pat. No. 6,091,058 (Faries, Jr. et al.), U.S. Pat. No. 6,255,627 (Faries, Jr. et al.) and U.S. Pat. No. 6,371,121 (Faries, Jr. et al.) and U.S. Patent Application Publication No. 2003/0231990 (Faries, Jr. et al.). The disclosures in the above-mentioned patents and patent application publication are incorporated herein by reference in their entireties.

2. Discussion of the Related Art

Generally, Mayo stands are commonly utilized in operating rooms to support various instruments for surgical procedures. These types of stands typically include a vertical support with a horizontal tray in which the instruments are placed. In order to provide a sterile field for the instruments, a Mayo stand cover is generally employed and placed over the tray and a substantial portion of the vertical support. For example, U.S. Pat. No. 5,379,703 (Marshall) discloses a folded cover which may readily be transported and placed over the tray of a Mayo stand with little likelihood of becoming prematurely unfolded and being contaminated by contact with a non-sterile surface. The Mayo stand cover includes an elongated flat bag of sterilizable sheet material having an open bottom end and a closed top end, and sized to fit over the tray and a portion of the vertical support of the Mayo stand when unfolded. A cuff is formed over a portion of the bag at the open end. Sterile, gloved hands may be placed into the cuff for transporting the cover and slipping the cover over the Mayo stand. The remaining portion of the bag is folded so as to define a folded material portion adjacent to and outside the cuff. An element is provided for retaining and releasing the folded material portion prior to and during use of the bag as a cover, respectively.

Performance of medical or surgical procedures may be enhanced by the use of heated medical instruments. The medical instruments are typically warmed prior to commencing the procedure and generally reduce the adverse effects caused by substantial temperature differences between the patient body and the medical instrument. Since Mayo stands generally support the medical instruments without thermal treatment, an additional device is required to warm the medical instruments for a procedure. This tends to clutter the operating room or other facility hosting the medical procedure and increases procedure costs. The device further provides medical personnel with the additional tasks of operating and monitoring the device for a medical procedure, thereby complicating the procedure and increasing the risk of injury and/or complications for the patient.

OBJECTS AND SUMMARY OF THE INVENTION

Accordingly, it is an object of the present invention to thermally treat medical instruments via a medical instrument stand including a thermally treated tray to enhance performance of medical or surgical procedures.

It is another object of the present invention to detect the presence of solution and/or a leak within a drape container disposed in a thermally treated tray of a medical instrument stand and to control thermal treatment of the tray in accordance with detected drape container conditions.

Yet another object of the present invention is to employ a surgical drape including solution and/or leak sensors with a thermally treated tray of a medical instrument stand, where the stand includes circuitry that interfaces the drape to control thermal treatment of the tray in accordance with drape conditions detected by the sensors and circuitry.

The aforesaid objects may be achieved individually and/or in combination, and it is not intended that the present invention be construed as requiring two or more of the objects to be combined unless expressly required by the claims attached hereto.

According to the present invention, a medical instrument thermal treatment system in the form of a stand includes a thermally treated tray to thermally treat medical instruments. The stand includes a frame to support the tray, while a drape including a sensing device is disposed over the tray to form a drape container or receptacle within the tray for collecting a sterile medium. The tray is thermally treated to heat the sterile medium in order to warm medical instruments or other medical items placed in the tray. The sensing device provides a signal to the system indicating the presence of liquid and/or leaks within the drape container to facilitate control of system operation.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

BRIEF DESCRIPTION OF THE DRAWINGS

FIG. 2 is an exploded view in perspective of the medical instrument system and drape of FIG. 1.

DETAILED DESCRIPTION OF THE PREFERRED EMBODIMENTS

Figure 1:
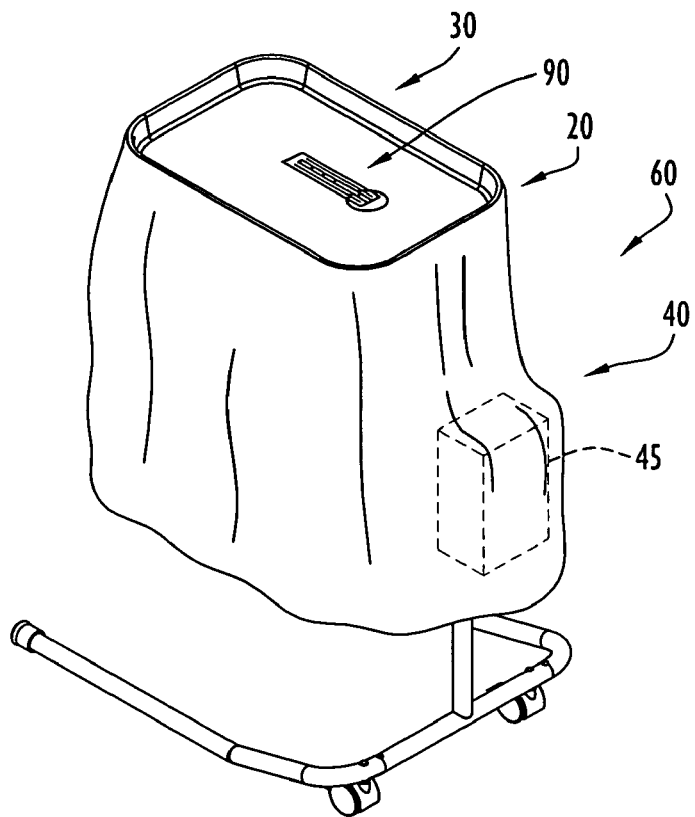
FIG. 1 is a view in perspective of a medical instrument thermal treatment system and drape for thermally treating medical instruments according to the present invention.

A medical instrument thermal treatment system according to the present invention is illustrated in FIGS. 1-2. The system is preferably in the form of a Mayo type stand utilized in operating rooms to support various instruments for surgical procedures. However, the system may be in the form of any type of stand or other support structure and may be utilized at any desired locations for various applications. Specifically, system or stand 60 includes a support or frame 40, a tray 20 supported by the frame, a surgical drape 30, a controller housing 45 and a heater 70. The frame includes a base 42, a support post 16 and a tray post 17. Base 42 is generally 'U'-shaped with substantially parallel legs 15 and a transverse leg 19 disposed between and connecting the parallel legs. The base typically includes casters or rollers 14 each disposed toward a corresponding opposing end of transverse leg 19. The casters support the base transverse leg to a raised position, while legs 15 each include an intermediate inclined leg section 39 to facilitate connection to and accommodate raised transverse leg 19.

Support post 16 is substantially cylindrical and is secured or attached to transverse leg 19 between casters 14. The support post extends upward from the transverse leg with controller housing 45 secured thereto toward a support post upper edge. The controller housing may be secured to the post via any conventional or other securing mechanisms (e.g., brackets, clamps, etc.). Controller housing 45 includes control circuitry (FIG. 4) including a power switch 46, a temperature controller 48, a power supply 54 and detection circuitry 100 to control system operation as described below.

Tray post 17 is substantially cylindrical and includes a post section 23 and a tray section 25 arranged in a generally 'L'-shaped configuration. The post section engages support post 16 as described below, while the tray section extends transversely from the post section and includes a tray bracket 21 secured thereto. The tray bracket is generally 'U'-shaped and includes a base member 29 with projections 27 each extending upward at a slight outward angle from a corresponding base member end. A wire type ring 18 is attached to the upper edge of each projection 27 and includes dimensions slightly less than those of portions of tray 20 to receive and support the tray within the ring. The ring is generally rectangular with each shorter dimensioned side attached to a corresponding projection. However, the ring may be of any size or shape and may be attached to the frame at any locations in any conventional or other fashion.

Post section 23 is attached or integral with tray section 25 and includes dimensions less than those of support post 16 to enable the post section to be inserted within the post. The post section and post basically form a telescoping arrangement to raise and lower tray 20 on the stand. A locking mechanism 28 is disposed on the support post above controller housing 45 to maintain post section 23 at a desired position within post 16. The locking mechanism may be implemented by any conventional or other locking devices (e.g., clamp, screw with the post section having corresponding openings defined therein, etc.). In other words, the locking mechanism enables tray 20 to reside at a desired height.

Tray 20 includes a floor 22 and side walls 24. The floor is generally rectangular with rounded corners, while side walls 24 extend upward from the floor peripheral edges at a slight outward angle. A lip or ledge 26 extends transversely outward from the wall upper edges and facilitates engagement with ring 18 to support the tray within the ring. The floor and side walls define a tray interior to contain surgical solution and instruments therein as described below. The tray is typically constructed of thermally conductive materials, however, the tray may be constructed of any suitable materials and may be of any shape or size. In addition, the tray may include any type of cover to further ensure maintenance of a sterile field for solution and instruments contained therein.

Heater 70 is disposed on the underside and/or sides of the tray to heat the tray and the sterile medium and instruments contained therein. The heater may include insulating materials to insulate the heater from surrounding components (e.g., frame 40, etc.). The heater is controlled by temperature controller 48 in accordance with an entered desired temperature and temperatures measured by a temperature sensor 72 (FIG. 4) as described below. Heater 70 is typically implemented by a conventional etched foil silicon rubber heating pad and is attached to the tray underside via a pressure sensitive or other type of adhesive. The heater is generally rectangular to substantially cover the tray underside and may include an open intermediate section and a recessed edge portion to accommodate tray bracket 21 and/or tray post 17. The heater may alternatively be of any quantity (e.g., at least one), shape or size, and may include any configuration (e.g., strips, bars, segments, etc.) that covers the entirety or any portion of the tray. In addition, the heater may be implemented by any conventional or other type of heater or heating element (e.g., heating coils, etc.) that may be disposed on the tray at any suitable locations.

Temperature sensor 72 (FIG. 4) is preferably implemented by a conventional resistive temperature device (RTD) (e.g., a 1,000 Ohm RTD). However, the sensor may be implemented by any conventional or other type of temperature sensor, and may be disposed at any suitable location on or in close proximity to the tray and/or heater. The temperature sensor is coupled to temperature controller 48 and may measure the temperature of the heater, liquid and/or tray. The temperature controller utilizes the measured temperature to control system operation as described below.

Sterile drape 30 is typically disposed over the stand and made to conform to the side walls and bottom of tray 20. The drape hangs down from the tray and covers controller housing 45, where power switch 46 and temperature controller 48 are adjustable manually through drape 30. The portion of drape 30 disposed in tray 20 serves as a sterile container or receptacle for sterile liquid and medical instruments placed therein to be heated. Typical sterile liquid treated by the stand is a 0.80% to 0.95% sodium chloride solution (i.e., saline). Drape 30 is made from materials that are impervious to the sterile liquid and sufficiently soft and flexible to conform to the tray walls. The thickness of the drape is preferably minimized to render thermal transfer therethrough most efficient, yet the thickness is sufficient to resist tearing and puncturing during normal use. The drape may be made of materials commonly used in hospitals for surgical drapes, or may be made of polyurethane film as disclosed for the drape in U.S. Pat. No. 4,934,152 (Templeton). The drape may further include a preformed container portion contoured to match the contour of the tray and/or a preformed controller portion contoured for placement over the controller housing. The preformed portions may be (but are not necessarily) thicker than the remaining portions of the drape described above in order to resist puncture and enable the preformed portions to maintain the shape of the tray and controller housing, respectively. By way of example only, the preformed portions may be made of a heavy gauge polyethylene/ionomer resin blend. The percentage of ionomer resin in the blend is typically (but not necessarily) in the approximate range of forty to seventy percent. The drape is designed to be disposable after a single use to enhance patient safety and is provided presterilized and prepackaged in a manner to preserve its sterile state during storage.

The drape is typically positioned over the stand with a portion of the drape disposed in the tray to form a drape receptacle as described above. The drape hangs down from the tray to cover the controller housing as described above. The drape forms a sterile field above the tray to maintain sterility of the sterile medium and medical instruments. However, a puncture, tear or other opening in the drape disrupts the sterile field and may contaminate the sterile liquid and instruments, thereby risking injury to a patient. Further, the stand may damage the drape (e.g., via the heating device) in the event that liquid is not present within the drape container.

Figure 3A:
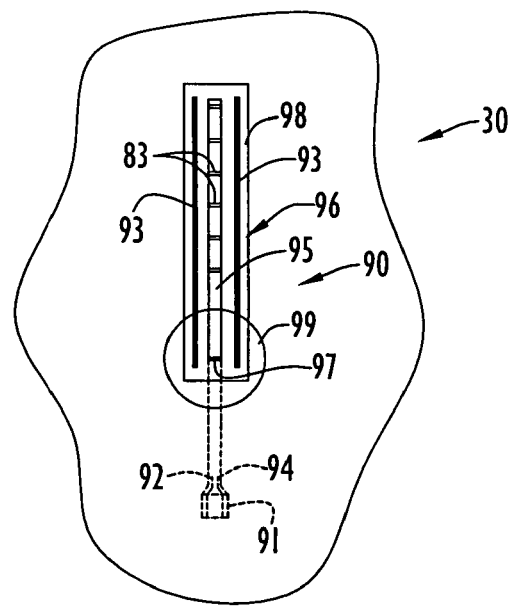
FIG. 3A is a top view in elevation of a portion of the drape of FIG. 2 including a sensing device extending therethrough and sealed with a patch disposed on the sterile drape surface.

In order to detect the presence of liquid and/or leaks within the drape container to maintain drape integrity and sterility of the sterile medium and medical instruments, drape 30 includes a sensing device as illustrated in FIG. 3A. Specifically, drape 30 is substantially rectangular and includes a sensing device 90 to detect the presence of liquid and leaks within a drape container. Sensing device 90 is in the form of a pair of electrodes 92, 94 that are affixed to a generally rectangular strip 95 disposed on an intermediate portion of the drape sterile surface. The electrodes are disposed on the electrode strip toward respective strip longer dimensioned edges and extend substantially in parallel. The electrode strip is enclosed within a pouch 96 to secure the electrodes to the drape and to protect the electrodes from sharp objects (e.g., medical instruments, etc.) that may be disposed within the tray. In addition, the pouch assists to prevent grounding of the electrodes or formation of a current flow path therebetween due to placement of conductive objects (e.g., medical instruments, etc.) in the tray that may produce erroneous detections. The pouch is formed from a substantially rectangular segment or flap 98 that is attached (e.g., welded, etc.) to the drape sterile surface and sealed by seams 93, each formed toward and extending along a respective flap longer dimensioned edge.

The distal ends of the electrodes are attached to a plug or connector 91 that interfaces detection circuitry 100 (FIG. 4) within controller housing 45 as described below. The plug includes electrode traces disposed on a plug top surface. The distal portions of strip 95 and electrodes 92, 94 pass through the drape from the sterile to the non-sterile drape sides via an opening or slit 97 defined in the drape at an intermediate location. A substantially circular segment or patch 99 is attached to the sterile drape surface to seal opening 97. The patch basically encompasses opening 97 and effectively seals that opening to prevent escape of liquid from, and maintain sterility of, the drape container. Flap 98 and patch 99 are preferably constructed of drape materials, however, the flap and patch may be constructed of any suitable materials, may be of any shape or size, and may be disposed on the drape at any suitable locations via any conventional or other techniques.

Sensing device 90 detects the presence of liquid and leaks within the drape container in response to placement of drape 30 over the tray. In particular, current flow between the electrodes is initiated in response to the electrodes contacting liquid. The current flow causes a respective change in voltage that indicates a condition and is detected by the detection circuitry within the controller housing as described below. In order to enable the liquid in the drape container to contact the electrodes and facilitate current flow between those electrodes, flap 98 includes a series of slots 83. The slots are defined in the flap between seams 93 and are spaced from each other in a direction of the flap longer dimension. The slots are generally rectangular and extend substantially perpendicular to electrodes 92, 94. Each slot includes a longer dimension substantially similar to the width of strip 95 and encompasses portions of each electrode 92, 94 to facilitate enhanced exposure of the electrodes to liquid within the drape container. Alternatively, flap 98 may include a series of substantially circular openings (not shown) defined therein to permit contact between the liquid and electrodes. Flap 98 may include any quantity of slots or openings of any shape or size and disposed at any locations in any desired fashion to facilitate contact between the electrodes and liquid within the drape container.

Figure 3B:
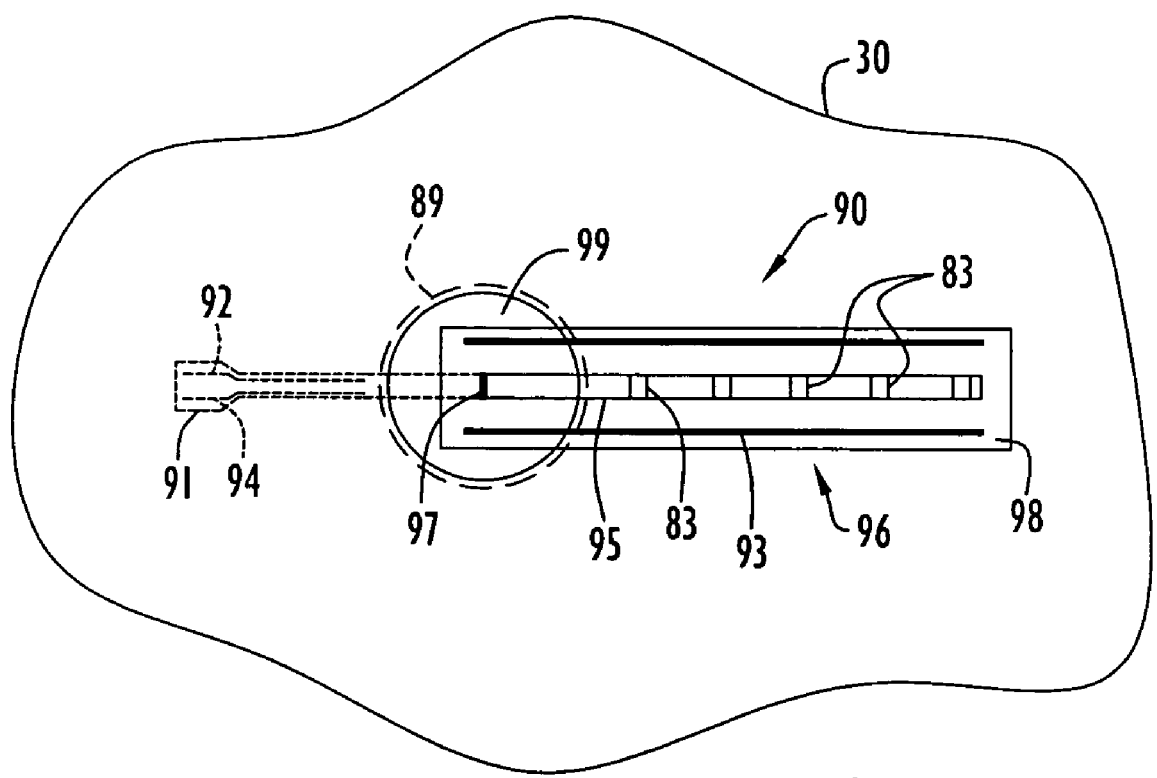
FIG. 3B is a top view in elevation of a portion of an alternative embodiment of the drape of FIG. 2 including the sensing device extending therethrough and sealed with a plurality of patches disposed on opposing drape surfaces.

An alternative embodiment of the drape employing patches on opposing drape surfaces to effectively seal the opening is illustrated in FIG. 3B. Initially, drape 30 and sensing device 90 are substantially similar to the drape and sensing device described above for FIG. 3A, except that two substantially circular segments or patches 89, 99 are attached to the drape to seal opening 97. Specifically, the drape includes sensing device 90 with electrodes 92, 94 disposed through opening 97 to pass between the drape sterile and non-sterile surfaces as described above. Patch 99 is attached to the sterile drape surface and encompasses opening 97 and a portion of sensing device pouch 96 as described above. Patch 89, substantially similar to patch 99, is attached to the non-sterile drape surface substantially coincident patch 99 to seal opening 97. Patches 89, 99 basically encompass opening 97 and effectively seal the opening to prevent flow of liquid from the drape container. The electrodes basically extend through opening 97 (e.g., and along a non-sterile drape surface) to facilitate connection of plug 91 to a receptacle 49 (FIG. 2) of controller housing 45 as described below. The electrodes provide signals to the detection circuitry to facilitate detection of liquid and/or leaks within the drape container as described above. The drape embodiments described above may employ opening 97 and sensing device 90 at any suitable locations on the drape coincident any portions of the tray or stand, and may employ any quantity of patches on any drape surfaces to seal opening 97. The stand may be utilized in combination with any of the drape embodiments described above.

Current flow between the electrodes (FIGS. 3A-3B) is initiated in response to the electrodes contacting liquid, where the current flow causes a respective change in voltage that indicates the presence of solution within the drape container. Further, the presence of a leak within the drape container enables current to flow between the electrodes and ground (e.g., the tray beneath the drape). The detection circuitry within the controller housing measures the voltage of and between the electrodes to determine drape container conditions. In particular, the detection circuitry initially applies a reference voltage or potential to electrodes 92 and/or 94. Since the electrodes are electrically isolated from each other within strip 95 as described above, current flow between the electrodes is prevented and the potential of and between those electrodes basically remains unchanged. Further, absence of the reference potential (e.g., minimal or no voltage on and between electrodes 92, 94) generally indicates the absence of a drape on the stand.

When the sterile medium is placed in the drape container, the sterile medium contacts electrodes 92, 94, thereby forming an electrical path or conductive bridge between those electrodes. Accordingly, current flow between the electrodes is initiated in response to the electrodes contacting liquid, thereby causing a change in the potential of and between electrodes 92, 94. Further, the presence of a leak within the drape container enables current to flow between the electrodes and ground (e.g., the tray beneath the drape), thereby causing a further change in the potential of and between electrodes 92, 94. The current flow (or lack thereof) resulting from each of the above conditions (e.g., absence of a drape, absence of solution, presence of solution, presence of a leak, etc.) is detected by the detection circuitry within the controller housing. This is typically accomplished by detecting the potential or voltage of and between electrodes 92, 94. The magnitude of the voltage or voltage change is utilized by the detection circuitry to detect the presence of the drape and/or the presence of solution and/or leaks within the drape container and to control system operation in accordance with the detected conditions as described below. For example, the detection circuitry may disable thermal treatment of the tray in response to the absence of liquid and/or drape or the presence of a leak within the drape container.

Figure 4:
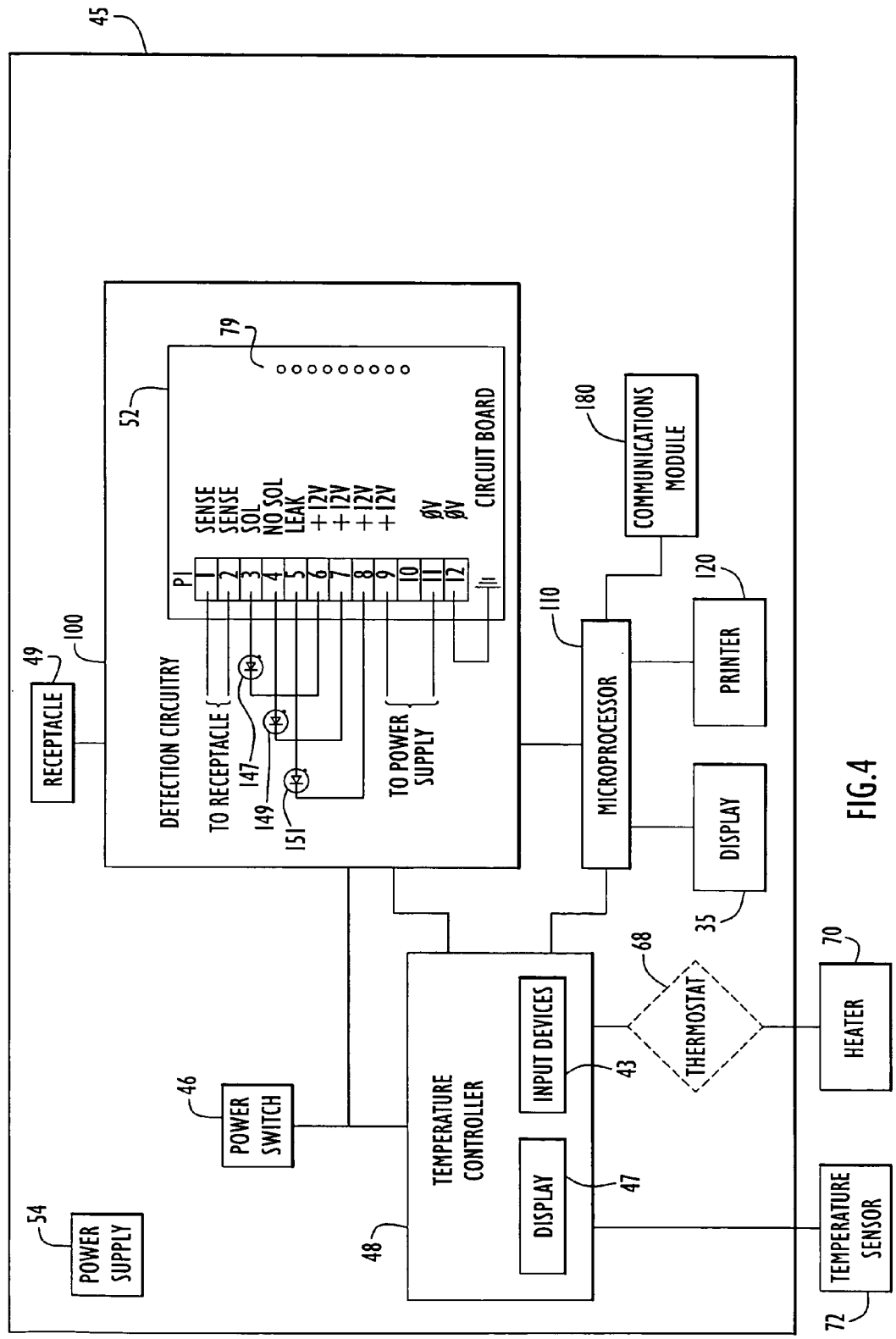
FIG. 4 is block diagram of control circuitry for the system of FIG. 1.

The detection circuitry within controller housing 45 receives signals from electrodes 92, 94 and controls system operation accordingly as described below. Referring to FIGS. 2 and 4, controller housing 45 is in the form of a generally rectangular box and houses control circuitry including power switch 46, temperature controller 48, receptacle 49, power supply 54 and detection circuitry 100. The power switch, temperature controller and receptacle are each disposed on a controller housing top surface, while detection circuitry 100 is disposed within the housing interior. Power supply 54 provides appropriate power signals to the housing components and includes a receptacle to receive signals from a power cord interfacing a conventional wall outlet jack. The power switch enables power to the housing components and may be implemented by any conventional or other switching device. Plug or connector 91 is received in receptacle 49 to provide electrode signals to the detection circuitry. This further enables the detection circuitry to detect the presence of a drape on the stand as described above. The temperature controller controls the heater, while the detection circuitry determines the drape container conditions based on the electrode signals and controls the temperature controller accordingly. The controller housing may further include audio and/or visual indicators 41 (e.g., beeper or buzzer, speaker 197 (FIG. 5), various colored light emitting diodes (e.g., a green diode 147, a yellow diode 149 and a red diode 151), etc.) disposed on the housing top surface to indicate drape container conditions. The detection circuitry may selectively actuate the indicators in any fashion to indicate the particular determined drape container conditions (e.g., absence of the drape or solution, the presence of a leak, etc.). The controller housing components may be disposed on and/or within the housing in any fashion at any desired locations.

Temperature controller 48 is connected to heater 70 and temperature sensor 72 to control the heater in response to a desired or set point temperature entered by a user and the temperature measured by the temperature sensor. In particular, temperature controller 48 is typically implemented by a conventional temperature controller or microprocessor and includes a display 47 and input devices 43 (e.g., buttons, keys, etc.). The temperature controller controls power to the heater based on a comparison of the temperature measured by temperature sensor 72 and the set point temperature entered by the user via input devices 43. The temperature controller may further display the measured and/or set point temperatures or any other desired information on display 47. The information to display may be selected by a user via input devices 43. When the measured temperature exceeds the set point temperature, controller 48 disables or reduces power to the heater. Conversely, when the measured temperature is below the set point temperature, controller 48 enables or increases power to the heater. A thermostat 68 may be disposed between the controller and heater to disable current to heater 70 in response to a temperature measurement exceeding a temperature threshold. The thermostat disables the heater in response to detection of excessive heater temperatures and may be implemented by any conventional switching type or limiting devices, such as a high limit thermostat, and disposed at any suitable location.

Temperature controller 48 further controls heater 70 in response to signals received from detection circuitry 100. The detection circuitry detects the presence of solution and leaks within the drape container and provides appropriate signals to temperature controller 48. The detection circuitry basically disables the temperature controller (and heater) in response to absence of the drape, absence of solution within the drape container and/or the presence of a drape container leak as indicated by the electrode signals. The detection circuitry may be substantially similar to the detection circuitry disclosed in the aforementioned patent applications. Alternatively, the detection circuitry may include a microprocessor to process electrode signals and control the indicators, heater or any other devices. In this case, electrode signals are converted to digital signals and compared by the microprocessor to threshold levels for each condition. The microprocessor may generate the appropriate control signals to control tray thermal devices and various indicators in accordance with the determined conditions. The microprocessor may be implemented by or implement the temperature controller and/or processor 110 described below.

Exemplary detection circuitry for stand 60 includes a circuit board 52 including a condition circuit 53 and green, yellow and red diodes 147, 149, 151 indicating the drape container conditions. The circuit board further includes a series of pins or terminals 1-12 to facilitate connections and a plurality of indicator lights 79. By way of example only, pins 1 and 2 are connected to controller housing receptacle or connector 49 to receive electrode signals, while pins 9 and 11 are connected to the positive and reference terminals of power supply 54, respectively. Pins 6-8 are connected to pin 9 and provide a voltage (e.g., +12V DC) to the condition circuit, while pin 12 is connected to pin 11 and provides a ground. Green diode 147 is connected between pins 3 and 6 and is illuminated in response to detection of solution within the drape container without a leak, while yellow diode 149 is connected between pins 4 and 7 and is illuminated in response to detection of the absence of solution and a leak within the drape container. Red diode 151 is connected between pins 5 and 8 and is illuminated in response to detection of a leak within the drape container. Pin 10 is basically inoperable and utilized to facilitate compatible connections with the board.

Figure 5:
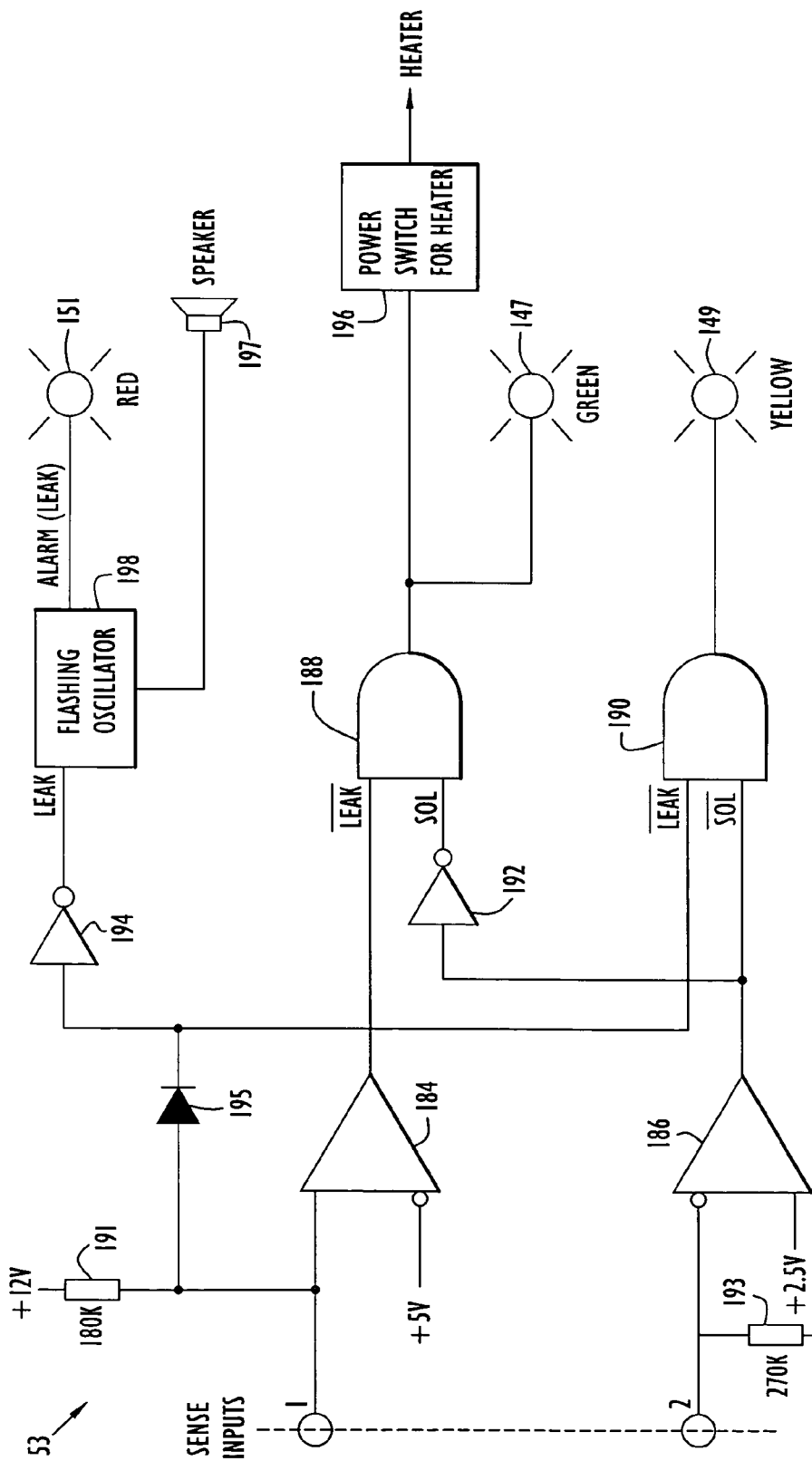
FIG. 5 is a schematic block diagram of an exemplary condition circuit of the detection circuitry within the control circuitry of FIG. 4 for determining the presence of liquid and/or leaks within a drape container.
Figure 6A:
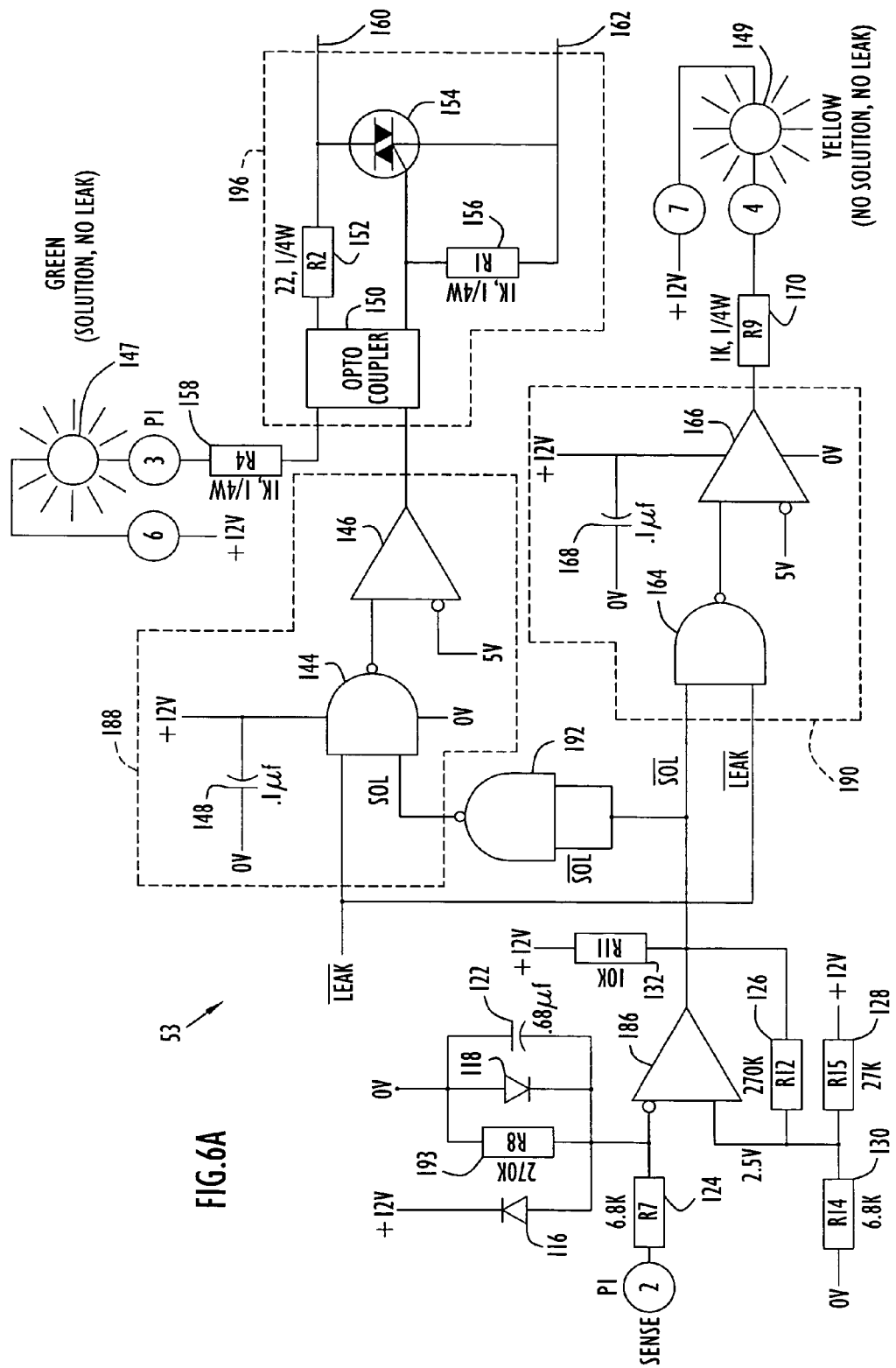
FIGS. 6A-6B are detailed electrical schematic diagrams of the exemplary condition circuit of FIG. 5.
Figure 6B:
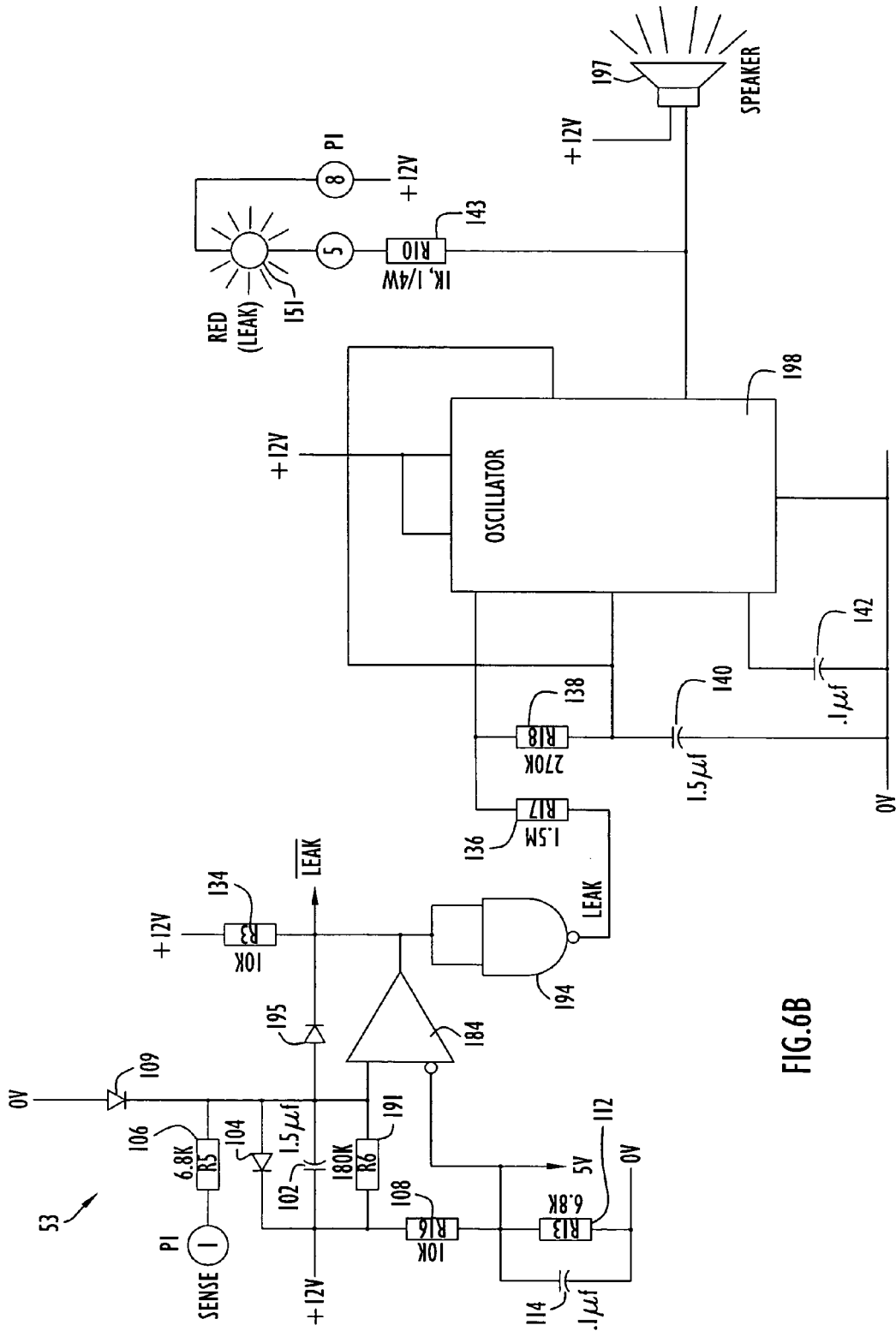

An exemplary condition circuit 53 for detecting the presence of solution and leaks within the drape container is illustrated in FIGS. 5, 6A and 6B. Initially, the condition circuit prevents operation of the thermal treatment system in the event a drape is damaged (e.g., contains a leak) or not connected to the detection circuitry, or in the event solution is absent from the drape container. The condition circuit is coupled to the drape electrodes via pins 1 and 2 of circuit board 52. The presence of solution within the drape container causes current flow between the electrodes, while a leak facilitates current flow between the electrodes and ground as described above. Accordingly, the current flow causes a voltage change at pins 1 and 2 of the circuit board, thereby enabling detection of solution and leaks by the condition circuit. In particular, the condition circuit includes comparators 184, 186, logic circuitry 188, 190, inverters 192, 194, a power switch 196 and an oscillator 198. Pin 1 of circuit board 52 is connected to the non-inverting input of comparator 184, while that input is further connected to a resistor 191 (e.g., 180K Ohm) disposed in series with a supply voltage (e.g., 12V DC). The non-inverting input of comparator 184 is further coupled to additional circuitry (FIG. 6B) (e.g., a resistor 106 (e.g., 6.8K Ohm) connected in series with pin 1, a resistor 108 (e.g., 10K Ohm) coupled to resistor 191 and the supply voltage, a diode 104 connected in parallel with resistor 191, a capacitor 102 (e.g., 1.5 μf) connected in parallel with resistor 191 and diode 104, and a diode 109 connected between the input and a ground potential) to protect the circuit from damage in the event an external voltage is applied to pins 1 and 2 and to provide filtering to prevent a response to noise. A diode 195 is disposed in a feedback path of comparator 184 to maintain the state of a particular condition as described below. The inverting input of comparator 184 is similarly coupled to additional circuitry (FIG. 6B) (e.g., a resistor 112 (e.g., 6.8K Ohm) connected between resistor 108 and a ground potential, and a capacitor 114 (e.g., 0.1 μf) connected in parallel with resistor 112) to enhance circuit performance. Resistors 108 and 112 basically provide the comparator inverting input with a reference voltage (e.g., 5V DC). Comparator 184 determines the presence of a drape container leak by comparing the input of pin 1 to the reference voltage (e.g., 5V DC). If pin 1 exceeds the reference voltage, the comparator provides a high level logic signal indicating the absence of a leak (e.g., the signal $\overline{LEAK}$ in the figures indicates the absence of a drape container leak when attaining a high logic level); otherwise a low level logic signal indicating the presence of a leak is produced by the comparator.

Pin 2 is connected to the inverting input of comparator 186, while that input is further connected to a resistor 193 (e.g., 270K Ohm) disposed between the comparator input and a ground potential. The inverting input is further coupled to additional circuitry (FIG. 6A) (e.g., a resistor 124 (e.g., 6.8K Ohm) connected in series with pin 2, a diode 116 connected in series with a supply voltage (e.g., 12V DC), a diode 118 connected in parallel with resistor 193, and a capacitor 122 (e.g., 0.68 μf) connected in parallel with resistor 193 and diode 118) to protect the circuit from damage in the event an external voltage is applied to pins 1 and 2 and to provide filtering to prevent a response to noise. The non-inverting input of comparator 186 is coupled to additional circuitry (FIG. 6A) (e.g., a resistor 126 (e.g., 270K Ohm) connected in a comparator feedback path, a resistor 128 (e.g., 27K Ohm) connected between the non-inverting input and a supply voltage (e.g., 12V DC), a resistor 130 (e.g., 6.8K Ohm) connected between the non-inverting input and a ground potential, and a resistor 132 (e.g., 10K Ohm) connected between a supply voltage (e.g., 12V DC) and the comparator output) that basically provides a reference voltage (e.g., 2.5V DC) for the comparator non-inverting input. Comparator 186 determines the presence of solution within the drape container by comparing the input of pin 2 with the reference voltage. If the reference voltage (e.g., 2.5V) exceeds pin 2, the comparator produces a high level logic signal indicating the absence of solution within the drape container (e.g., the signal $\overline{SOL}$ in the figures indicates the absence of solution within the drape container when attaining a high logic level); otherwise a low level logic signal indicating the presence of solution is produced.

The output of comparator 184 is coupled to inverter 194, to an input of logic circuitry 188 and to an input of logic circuitry 190. The comparator output is further coupled to additional circuitry (FIG. 6B) (e.g., a resistor 134 (e.g., 10K Ohm) connected between the comparator output and a supply voltage (e.g., 12V DC)) to enhance circuit performance. Inverter 194 is in the form of a NAND gate (FIG. 6B) and inverts the comparator output. Since comparator 184 provides a low level logic signal in response to the presence of a leak as described above, inverter 194 inverts the comparator output to provide a high level logic signal in response to a leak (e.g., the signal LEAK in the figures indicates the presence of a drape container leak when attaining a high logic level). The inverter is connected to a timer 198 that serves as a low frequency oscillator and is actuated by the high level logic signal produced by inverter 194 in response to the presence of a leak. Additional circuitry (FIG. 6B) (e.g., a resistor 136 (e.g., 1.5M Ohm) connected in series with the NAND gate output, a resistor 138 (e.g., 270K Ohm) connected between timer inputs, a capacitor 140 (e.g., 1.5 μf) connected between resistor 138 and a ground potential, and a capacitor 142 (e.g., 0.1 μf) connected between a timer input and the ground potential) is connected to and/or between the inverter and oscillator to enhance actuation of the oscillator in response to a high level logic signal from the inverter. The oscillator output is coupled to a reference terminal of a speaker 197 and to pin 5 for actuating red diode 151. A resistor 143 (e.g., 1K Ohm) is disposed between pin 5 and the oscillator output, while a speaker positive terminal is connected to a supply voltage (e.g., 12V DC). The oscillator output is in the form of a pulse train that provides periodic low level logic signals. The low level signals provide a sufficient voltage differential to enable the supply voltages of the red diode (e.g., 12V DC of pin 8) and speaker (e.g., 12V DC of the speaker positive terminal) to drive those devices. Thus, the oscillator produces a pulse train that enables the diode to flash and the speaker to beep at rates proportional to the pulse train frequency when a leak is present in the drape container.

Conversely, when a leak is absent from the drape container, comparator 184 provides a high level logic signal as described above. Inverter 194 inverts the comparator output to provide a low level logic signal in response to the absence of a leak. The low level logic signal is insufficient to actuate oscillator 198, thereby disabling red diode 151 and speaker 197 when a leak is not present within the drape container.

Logic circuitry 188 determines the presence of conditions to enable the heater (e.g., solution is present within the drape container without a leak). The logic circuitry is coupled to outputs of comparators 184 and 186. An inverter 192 in the form of a NAND gate (FIG. 6A) is disposed between logic circuitry 188 and comparator 186 to invert the comparator output. Since comparator 186 produces a low level logic signal in response to the presence of solution within the drape container, inverter 192 inverts the comparator output to provide a high level logic signal in response to the presence of solution (e.g., the signal SO L within the figures indicates the presence of solution within the drape container when attaining a high logic level). Logic circuitry 188 combines the signals (e.g., $\overline{\text{LEAK}}$, SOL) from comparator 184 and inverter 192, indicating leak and solution conditions, and provides a signal to illuminate green diode 147 and actuate power switch circuitry 196 to enable heater 70 in response to the signals indicating the presence of solution without a leak in the drape container.

Logic circuitry 188 (FIG. 6A) includes a NAND gate 144 and a comparator 146. The NAND gate receives output signals from comparator 184 and inverter 192 and produces a low level logic signal in response to the signals indicating the presence of solution in the drape container without a leak. The NAND gate output is connected to the non-inverting input of comparator 146, while the comparator inverting input is connected to a reference voltage (e.g., 5V DC). The comparator produces a low level logic signal in response to a low NAND gate output in order to drive power switch circuitry 196 to enable heater 70 when solution is present within the drape container without a leak. NAND gate 144 is further coupled to additional circuitry (e.g., a ground potential coupled to a gate terminal, a supply voltage (e.g., 12V DC) coupled to another gate terminal with a capacitor 148 (e.g., 0.1 μf) connected between that gate terminal and a ground potential) to enhance gate operation.

Power switch circuitry 196 includes an optocoupler 150 and a triac 154. The triac is connected between conductors 160, 162 that provide signals to temperature controller 48, and has a gate terminal coupled to an output of the optocoupler. An optocoupler input is coupled to circuit board pin 3 and, hence, to green diode 147 disposed between circuit board pins 3 and 6, while a resistor 158 (e.g., 1K Ohm) is connected between pin 3 and the optocoupler. The output of comparator 146 indicating drape container conditions is connected to another input of the optocoupler to drive the power switch circuitry in response to the presence of solution without a leak in the drape container as described above. A resistor 152 (e.g., 22 Ohms) is connected to an optocoupler output and in series with the triac, while a resistor 156 (e.g., 1 K Ohm) is connected between the triac gate terminal and conductor 162. A low level logic signal produced by comparator 146 provides a ground that enables the optocoupler input to receive appropriate current to produce outputs that drive the triac. Thus, the low level logic signal from comparator 146 enables actuation of the green diode and triac to indicate the presence of solution without a leak in the drape container and to enable the heater, respectively. The triac provides signals to temperature controller 48 to control actuation of the heater as described above.

Conversely, when a leak is present within, or solution is absent from, the drape container, comparators 184, 186 provide signals that enable NAND gate 144 to produce a high level logic signal. Comparator 146 generates a high level logic signal in response to the high level NAND gate output, thereby preventing actuation of power switch 196, green diode 147 and heater 70 when a leak is present within, or solution is absent from, the drape container.

Logic circuitry 190 determines the presence of conditions to illuminate yellow diode 149 (e.g., neither solution nor a leak is present within the drape container). The logic circuitry is coupled to the outputs of comparators 184 and 186. Logic circuitry 190 combines the signals (e.g., $\overline{\text{LEAK}}$, $\overline{\text{SOL}}$) from comparators 184, 186 indicating drape container conditions and provides a signal to actuate yellow diode 149 in response to the comparator signals indicating the absence of solution and a leak within the drape container.

Logic circuitry 190 (FIG. 6A) includes a NAND gate 164 and a comparator 166. The NAND gate receives output signals from comparators 184 and 186 and produces a low level logic signal in response to the comparator signals indicating the absence of solution and a leak within the drape container. The NAND gate output is connected to the non-inverting input of comparator 166, while the comparator inverting input is connected to a reference voltage (e.g., 5V DC). The comparator provides a low level logic signal in response to a low NAND gate output in order to illuminate yellow diode 149. The yellow diode is disposed between circuit board pins 4 and 7 with a resistor 170 (e.g., 1K Ohm) connected between pin 4 and the comparator output. A low level logic signal produced by comparator 166 provides a sufficient voltage differential to enable pin 7 connected to a supply voltage (e.g., 12V DC) to illuminate yellow diode 149. Conversely, when a leak or solution is present within the drape container, comparators 184, 186 provide signals that enable NAND gate 164 to produce a high level logic signal. Comparator 166 generates a high level logic signal in response to the high level NAND gate output, thereby preventing illumination of yellow diode 149 when a leak or solution is present within the drape container.

The condition circuit basically controls system operation in response to detected drape container conditions. The circuit is arranged to enable signals from comparators 184, 186 to selectively facilitate a particular action (e.g., illuminate the red diode and speaker, enable the green diode and heater, or illuminate the yellow diode) in response to the occurrence of corresponding conditions for that action. In other words, a particular action is initiated by the condition circuit in response to the occurrence of corresponding conditions, while remaining actions are disabled. Thus, the green diode and heater are enabled by the condition circuit in response to the presence of solution without a leak in the drape container, and are disabled during occurrence of other drape container conditions (e.g., a leak or no solution within the drape container). Enablement and disablement of the yellow diode and red diode and speaker are facilitated in a similar manner with respect to their corresponding conditions. The condition circuit and/or circuit board may further include circuitry to record the time and/or date when the system or heater is enabled and disabled or any other information. The stored information may be retrieved for hospital records or to assist in evaluating system performance.

The manner in which the condition circuit operates is described, by way of example only, with reference to FIGS.

4-5. Initially, when solution is absent from the drape container, no current flow exists between electrodes 92, 94 (FIGS. 3A-3B) and the voltage applied to pins 1 and 2 of circuit board 52 is maintained at twelve and zero volts, respectively. These conditions are similarly present when the drape is disconnected from or incompatible with the system. The output of comparators 184 and 186 are high (e.g., indicating no leak and no solution), thereby enabling logic circuitry 190 to illuminate yellow diode 149 as described above, while the heater, speaker and green and red diodes are disabled as described above.

In the event that solution is present without a leak in the drape container, a conductive path is formed between the electrodes and, hence, between pins 1 and 2 of the circuit board. Since the conductive path has a low resistance relative to resistors 191 and 193, these resistors basically form a voltage divider with resistor 191 connected to the supply voltage of 12V DC and resistor 193 connected to ground. The voltage divider provides each pin 1 and 2 with approximately 7.2 V DC. Accordingly, the output of comparator 184 is high (e.g., indicating no leak), while the output of comparator 186 is low (e.g., indicating the presence of solution), thereby enabling logic circuitry 188 to illuminate the green diode and actuate the power switch to enable the heater, while the speaker and red and yellow diodes are disabled as described above.

A leak within the drape container forms a conductive path between the electrodes (e.g., and, hence, pins 1 and 2) and ground. Thus, the potential of pin 1 is reduced below the comparator reference potential (e.g., 5V DC), thereby causing comparator 184 to produce a low level logic signal. Diode 195 provides feedback to maintain the state of the leak condition until power is disabled. The low output of comparator 184 is inverted by inverter 194, thereby actuating oscillator 198. The oscillator illuminates red diode 151 and actuates speaker 197 to provide an audio leak indication, while the heater and green and yellow diodes are disabled as described above. The output of comparator 186 has no bearing on leak detection and is ignored with respect to actuation of the oscillator. The condition circuit basically generates signals to control the heater and provides visual and audio indications to inform a user of the drape container status.

The condition circuitry may employ any conventional or other components that perform the above-described functions. The reference voltages utilized by comparators 184, 186 to detect drape container conditions may be any suitable voltages. By way of example only, the reference voltages utilized by those comparators in the condition circuit are derived from properties of saline or salt-water type solutions. Further, the reference voltages may be adjusted to account for objects placed in the basin. For example, placement of conductive objects (e.g., instruments, etc.) within the tray may establish a path for current flow between the electrodes irrespective of the presence of solution, thereby enabling the condition circuit to indicate erroneous conditions. Accordingly, the reference voltages may be adjusted to differentiate between current flow initiated by solution and the current flow initiated by a conductive object. Alternatively, conductive objects may be utilized in combination with and placed on a stand disposed within the tray to elevate the objects above the electrodes and basin floor in a manner similar to that disclosed in U.S. Pat. No. 6,087,636 (Faries, Jr. et al.).

In addition, the control circuitry may include devices to measure, record and/or provide a report (e.g., hardcopy or electronic form) of stand conditions (e.g., time, date, temperature, leak indication, etc.). The report provides medical personnel documentation for their files on the heating characteristics. The primary information produced is the start date and start time of solution heating, the time interval the solution was heated and the temperature the solution attained during heating (e.g., partial or complete history of time and solution temperature). The report may further include a variety of information (e.g., facility name and location, patient information, doctor information, type of procedure, type of solution and/or instruments being heated, amount of solution being heated, etc.). Referring back to FIG. 4, the control circuitry may further include a processor 110, a printer 120 and a communications module 180. These components may be implemented by any conventional or other components performing the functions described herein. Processor 110 is coupled to temperature controller 48 and detection circuitry 100 in order to receive information relating to the tray and/or heater temperature and drape container conditions. The processor may receive any additional information (e.g., facility information, doctor information, patient information, solution information, instrument information, etc.) from medical personnel or users via processor input devices (not shown).

The processor further maintains the date, elapsed heating time and occurrence time of an event or condition (e.g., the time when a leak occurs, the time when instruments are inserted within the drape container, etc.). The processor may measure the elapsed time or record an occurrence time based on signals received from the temperature controller and/or detection circuitry. For example, the processor may initiate measurement of a time interval in response to the detection circuitry indicating solution within the drape container, and may store the elapsed and/or occurrence time in response to a leak or other condition. The processor may further measure elapsed time or record elapsed and/or occurrence time in response to medical personnel manually entering information on the processor input devices (e.g., start and stop keys). The processor collects the appropriate information and arranges the information into a report. The report may be arranged in any fashion and include any desired information. Moreover, the report and/or information may be stored in a database or memory device (e.g., local memory, removable memory, card, disk, etc.) for later retrieval. In addition, the processor is coupled to a processor or stand display 35 to display the elapsed (or running) time, report or any desired information to medical personnel. The information displayed may be selected via the processor input devices, or the display may include display controls (e.g., buttons, keys, etc.). Display 35 may be disposed on the controller housing top surface (FIG. 2) or at any other desired stand location.

The processor is further coupled to printer 120 and communications module 180 in order to provide information to a user. The printer basically provides a report in hardcopy form. The processor may control the printer to produce the report at specified times (e.g., termination of heating, at particular times of day, after a particular quantity of uses, etc.) or in response to requests from medical personnel via processor input devices (e.g., print key). The printer may print the report on any desired hardcopy medium. Preferably, the printer places the information onto a label that is attached to a medical file. The information may be printed during or after the solution heating, or be stored on a memory device and printed at a desired time as described above. The printer may further provide additional copies of the report in response to user requests, or a medium automatically creating duplicates may be utilized (e.g., carbon-less paper, etc.). Controller housing 45 includes a slot 37 (FIG. 2) to provide the printed report to a user. However, the slot may be defined at any desired location. Since the controller housing is under the drape adjacent the non-sterile drape side (e.g., the controller housing is non-sterile), the printed report is typically retrieved from the controller housing after completion of the medical procedure (e.g., when the drape is discarded) to preserve sterility.

Communications module 180 enables the report to be provided in electronic form. This module basically facilitates communication with other devices for transference or downloading of the report to those devices. For example, the information may be downloaded or transmitted over a network or other communications medium to another device (e.g., PDA, computer, another stand, etc.) for viewing, storage and/or printing. Moreover, the communications module may facilitate retrieval of information (e.g., patient information, facility information, doctor information, solution information, instrument information, etc.) from a database or other source for the report.

Operation of the instrument stand is described with reference to FIGS. 1-4. Initially, drape 30 is placed over stand 60 and disposed in tray 20 to form a drape receptacle. Electrode strip 95 of the drape is coupled to controller housing 45 to connect the drape to the detection circuitry to facilitate detection of drape container conditions. The detection circuitry initially senses no voltage change across the electrodes, thereby indicating the absence of solution and a leak within the drape container (e.g., the absence of an electrical path between the electrodes) as described above. An indicator 41 (e.g., yellow diode 149) may be actuated to indicate this condition, while thermal treatment of the tray is disabled.

A sterile medium and one or more instruments are disposed within the drape receptacle and a desired temperature for the medium is entered into controller 48 by the user via input devices 43. The sterile medium forms a conductive path between the electrodes that affects the voltage across the electrodes as described above. The detection circuitry senses the voltage change indicating the presence of solution without a leak in the drape container, and may actuate a corresponding indicator 41 (e.g., green diode 147). Temperature controller 48 subsequently controls thermal treatment of the tray and may display system information on display 47 as described above. In addition, processor 110 may receive information from the temperature controller and/or detection circuitry to start measuring a heating time interval and collect report information as described above. The elapsed time or other information may be displayed on display 35 as described above.

When a leak occurs within the drape container, an electrical path is formed between the electrodes and the tray serving as ground, thereby affecting the voltage between the electrodes as described above. The detection circuitry senses the voltage change indicating a leak within the drape container and disables thermal treatment of the tray. A corresponding indicator 41 (e.g., red diode 151) may be actuated to indicate this condition. Further, processor 110 may receive information from the temperature controller and/or detection circuitry to record the elapsed and/or occurrence time as described above.

Processor 110 may receive appropriate information for a report from the temperature controller, detection circuitry and/or processor input devices at any time (e.g., before, during or after the heating session). The processor arranges the information into a desired report as described above. The report may be produced by printer 120 or transmitted to another device via communications module 180 as described above. The report may be generated in response to termination of a session (e.g., indicated by signals received by processor 110 from the temperature controller and/or detection circuitry) or a request by medical personnel (e.g., via processor or other input devices).

It will be appreciated that the embodiments described above and illustrated in the drawings represent only a few of the many ways of implementing a heated medical instrument stand with surgical drape and method of detecting fluid and leaks in the stand tray.

The stand may be of any type (e.g., Mayo, etc.), shape or size and may be constructed of any suitable materials. The stand may be utilized at any desired locations (e.g., locations where medical procedures may be conducted, hospitals, operating rooms, outpatient facilities, doctor offices, etc.). The stand may include any quantity of heating and/or cooling trays in any combinations. The trays may receive any types of instruments or other objects. The frame and associated components (e.g., base, base legs, support post, tray post, tray bracket, ring, etc.) may be of any quantity, shape or size, may be constructed of any suitable materials and may be arranged in any fashion. The stand may alternatively include a housing to support the tray and associated stand components (e.g., control circuitry, heater, etc.). The casters may be of any quantity, shape or size, may be implemented by any conventional or other roller and may be disposed at any location. The stand may alternatively be implemented without casters. The controller housing may be of any quantity, shape or size, may be constructed of any materials and may be disposed at any location and include any control circuitry or other stand components. The locking mechanism may be implemented by any conventional or other locking mechanism to secure the tray height and may be disposed at any location.

The tray may be of any shape or size, may be constructed of any suitable thermal conducting materials (e.g., stainless steel, etc.) and may be disposed at any suitable locations on or within the frame. The tray may include any type of cover to enhance the sterile field and may contain any quantity of any type of medical or other instruments or objects. The tray may be removably or permanently secured to the stand in any desired fashion via any conventional or other fastening techniques (e.g., brackets, rings, clamps, etc.). The tray bracket may be of any shape or size, may be disposed at any suitable locations, may be constructed of any suitable materials and may be implemented by any conventional or other bracket. The ring may be of any shape or size, may be disposed at any suitable locations and may be implemented by any conventional or other ring.

The stand may include any conventional or other heating and/or refrigeration units to thermally treat the sterile medium and instruments or other objects to any desired temperature. The stand may utilize any desired fluids or solutions (e.g., saline, etc.) within the tray or drape container. The heater may include any conventional or other heating device and components to control heating of a tray to any desired temperature (e.g., preferably to temperatures near (e.g., above, at or below) body temperature, such as temperatures in the approximate range of 60° F.-160° F.). The heater may be of any quantity (e.g., at least one), shape or size, and may include any configuration (e.g., strips, bars, segments, etc.) that covers the entirety or any portion of a tray. The heater may be attached to a tray via any conventional or other fastening techniques (e.g., any type of adhesives, brackets, etc.). The stand may include any insulating materials disposed at any locations proximate the heater to insulate the heater from the stand or stand components. In addition, the heater may be implemented by any conventional or other type of heater or heating element (e.g., heating coils, etc.) that may be disposed on or proximate a tray at any suitable locations.

The temperature sensor may be implemented by any quantity of any conventional or other temperature sensing device (e.g., infrared, RTD, etc.) and may be disposed at any location on or proximate a tray or heater. The stand may thermally treat (e.g., heat or cool) any type of medium or liquid and/or objects (e.g., instruments, containers, etc.).

The controller housing may be of any quantity, shape or size, may be constructed of any suitable materials, and may be disposed at any suitable locations on the stand. The controller housing may include any suitable conductors or other medium (e.g., wireless, fiberoptics, etc.) to transfer signals between stand components. The controller housing may include any type of receptacle disposed at any suitable location on the controller housing or stand to interface the drape sensing device. The controller housing may include any quantity of any type of indicator (e.g., audio, speech synthesis, LED, display screen with text or images, etc.) to indicate the drape container status. The indicators may be disposed on the controller housing or stand at any suitable locations. The indicators may be actuated in any desired fashion, combination or pattern (e.g., flashing, continuous illumination, beep, continuous buzzer, etc.). A drape container or other condition may be associated with any quantity of any indicators (e.g., the same or different indicators in any desired combinations).

The drape may be of any size or shape, and may be constructed of any suitable materials. The drape is preferably transparent or translucent to facilitate manipulation of controls through the drape, however, these drapes may have any degree of transparency (e.g., including opaque). The drape may be manipulated in any fashion with any portions of the drape serving as a drape receptacle within a corresponding tray. The drape may be of sufficient size to accommodate and form drape receptacles within any quantity of trays.

The sensing device may include any quantity of electrodes or electrode strips disposed at any suitable locations on a drape. The electrodes may be constructed of any suitable conductive materials. The electrode strip may be of any shape or size, and may be constructed of any suitable materials. The electrodes may be fastened to the strip at any suitable locations via any conventional or other fastening techniques. The pouch may be of any quantity, shape or size, may be constructed of any suitable materials, may contain any portions of the electrodes or electrode strip and may be fastened to the drape at any suitable locations via any conventional or other fastening techniques. The flap may be of any quantity, shape or size, may be attached to the drape at any suitable locations via any conventional or other fastening techniques to form the pouch and may be constructed of any suitable materials. The seams may be disposed on the flap at any suitable locations to attach the flap to the drape to form the pouch. The flap may include any quantity of openings or slots of any shape or size disposed at any suitable locations on the flap or pouch and arranged in any fashion to enable liquid within the drape container to contact the electrodes. Alternatively, the sensing device or electrode strip may be attached to the drape (i.e., without the pouch) via the patch or any other securing mechanisms (e.g., adhesives, welding, etc.) to sense drape container conditions.

The drape opening may be of any quantity, shape or size and may be defined in the drape at any suitable locations (e.g., drape portions within the tray, near the controller housing, along the frame, etc.). The patch may be of any quantity, shape or size, may be constructed of any suitable materials and may be disposed at any suitable locations on the drape. The drape may include any quantity of openings and corresponding patches disposed on or attached to either or both of the sterile and non-sterile drape surfaces. The drape may include any quantity of sensing devices for a corresponding tray where the sensing device signals may be combined in any fashion (e.g., at least one device detecting liquid, combined logically (e.g., AND, OR, etc.), etc.) to determine occurrence of drape container conditions (e.g., solution or leaks present). The sensing device plug may be implemented by any conventional or other plug or connector where the electrode traces may be disposed at any locations on the plug. Alternatively, the electrode strip or other objects may traverse a drape peripheral or other edge (e.g., without being disposed through the drape) to extend between the sterile and non-sterile drape surfaces (e.g., FIG. 2).

Figure 7:
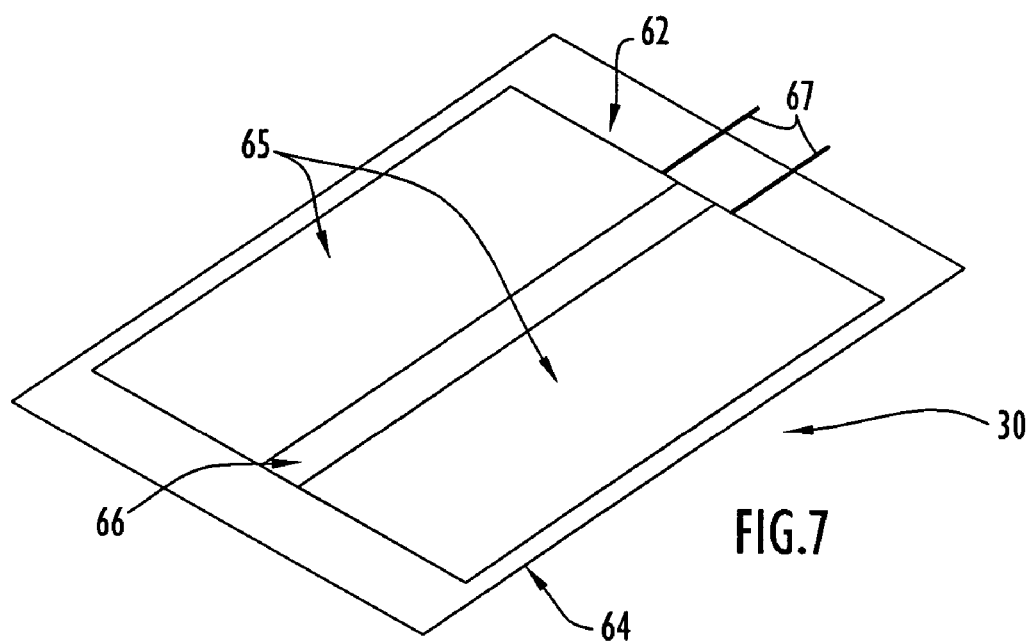
FIG. 7 is a perspective view of an alternative drape for the system of FIG. 1.

The drape may alternatively include one or more conductive layers to detect drape container conditions. For example, the drape (FIG. 7) may include a detection layer 62 and an insulating layer 64 attached thereto via any conventional or other techniques. The detection layer includes a plurality of conductive segments 65 and at least one insulating segment 66. The conductive segments are preferably constructed of polymeric materials with electrical conducting properties, while the insulating segment is preferably formed of conventional polymeric materials that have minimal or no electrical conducting properties. The segments are arranged to enable the insulating segment to electrically isolate the conductive segments. In other words, an insulating segment is typically disposed between adjacent conductive segments. The conductive and insulating segments may be of any shape or size and arranged in any fashion that electrically isolates the conductive segments from each other. The insulating layer isolates the detection layer from the tray and stand to prevent formation of electrical paths between conductive segments via the tray and/or stand. Leads or conductors 67 are connected to or integral with the conductive segments to couple the conductive segments to the detection circuitry. Current flow is initiated in response to liquid contacting the conductive segments and/or tray, thereby enabling the detection circuitry to determine drape container conditions based on the potential of and between the leads (or conductive segments) in substantially the same manner described above.

The control circuitry may be disposed within the controller housing or on the stand at any suitable locations and may be implemented by any conventional or other circuitry components arranged in any desired fashion to perform the described functions. The stand may be powered by any conventional or other power source (e.g., AC, DC, wall outlet jack, batteries, etc.). The temperature controller may be implemented by any quantity of any conventional or other temperature controller and include any quantity of any desired input devices (e.g., buttons, keypad, etc.). The power switch may be implemented by any conventional or other switching device. The temperature controller may control the heater to any desired temperature range, and may utilize any quantity of set points (e.g., maximum and/or minimum, etc.).

The detection circuitry may be disposed within the system at any suitable locations and may include any quantity of conventional or other components arranged in any desired fashion to perform the functions described herein. The detection circuitry may utilize any suitable reference potentials to detect solution, leaks or any other conditions. Drape container conditions may be determined based on any desired electrical or other parameters or characteristics (e.g., potential or voltage, current, resistance, etc.) of any quantity of electrodes. The parameters may be measured at any suitable locations (e.g., at any locations along each electrode, between the electrodes, between the electrodes and tray, at the tray, between the electrodes and detection circuitry, within the detection circuitry, etc.).

The electrical connections may include any quantity of components (e.g., power cord, fuses, conductors, connectors, power supply, circuit board, diodes, etc.) arranged in any desired fashion, where each component may be implemented by any conventional or other component performing the described function. The power cord may be implemented by any conventional or other cord or cable and be configured to accommodate any desired power signals. The thermostat may be implemented by any conventional switching type or limiting devices, such as a high limit thermostat, and may be disposed at any suitable location within the system.

The circuit board housing the condition circuit may include any quantity of terminals or pins each associated with any desired signals or portion of the condition circuit. The circuit board may include any quantity of indicators disposed at any suitable locations to indicate the occurrence or status of any desired circuit portion or condition. The power supply may be implemented by any conventional or other power supply or source and provide any desired power signals, and may include any type of conventional or other receptacle for receiving any type of plug or connector. The diodes or other indicators may be connected to the circuit board pins in any desired fashion. The circuit board may house the condition circuit and/or any other desired system circuitry. Further, the circuit board may include devices to record any types of information relating to system operation for subsequent retrieval and analysis (e.g., date and time of thermal treatment disablement and enablement, etc.).

The condition circuit may include any quantity of conventional or other components arranged in any desired fashion to perform the functions described herein. The circuit comparators may be implemented by any conventional or other comparators or comparing devices and may utilize any suitable reference potentials to detect solution, leaks or any other conditions. The inverters may be implemented by any conventional or other inverting devices (e.g., logic gates, circuitry, etc.) to invert circuit signals. The logic circuitry and corresponding logic gates may be implemented by any logic gates or combinational logic (e.g., AND, OR, NAND, NOR, XOR, etc.) and/or circuitry (e.g., comparator, inverter, transistors, etc.) arranged in any desired fashion to combine signals to determine the occurrence of any conditions. The logic circuitry comparators may be implemented by any conventional or other comparators or comparing devices and utilize any desired reference potentials. The oscillator may be implemented by any conventional or other timer or oscillating device producing outputs at any desired frequency. The oscillator may drive any type of device (e.g., speaker, speech synthesis, diode, etc.) to indicate the presence of a condition, while the indicator devices may alternatively be driven by any type of circuitry or mechanism. The speaker may be implemented by any conventional or other speaker or audio device and may provide any suitable audio indication (e.g., beep at any suitable periodic interval, continuous audio output, etc.).

The triac may be implemented by any conventional or other triac or relay type device to provide signals to the temperature controller for controlling thermal treatment of a tray. The condition circuit may include any conventional or other circuitry (e.g., resistors, capacitors, inductors, diodes, supply and ground potentials, etc.) arranged in any fashion and including any desired electrical characteristic values (e.g., resistance, potential, capacitance, etc.) to facilitate circuit operation. The condition circuit signals may include any desired logic or voltage levels. The optocoupler may be implemented by any conventional or other optocoupler or other circuitry to control the triac to provide signals to the thermal control circuitry.

A plural tray stand may include individual thermal control and detection circuitry associated with each tray to monitor drape container conditions and control tray operation. Alternatively, the plural tray stand may include common thermal control and detection circuitry to control each tray in response to drape container conditions. The common circuitry may receive signals from each sensing device and control the trays individually or collectively in response to the drape container conditions. The common circuitry may process and combine the signals in any fashion (e.g., AND, OR, etc.) to determine conditions for controlling the trays.

The detection circuitry may alternatively include a microprocessor to process electrode signals and control the indicators, heater or any other devices. In this case, electrode signals are converted to digital signals and compared by the microprocessor to threshold levels for each condition. The microprocessor may generate the appropriate control signals to control tray thermal devices and various indicators in accordance with the determined conditions. The microprocessor may be implemented by or implement the temperature controller and/or report processor.

The control circuitry may include devices to record any types of information relating to system operation for subsequent retrieval, analysis, display and reports (e.g., date and time of thermal treatment disablement and enablement, etc.). The processor may be implemented by any conventional or other microprocessor or controller and include any quantity of any desired input devices (e.g., buttons, keypad, etc.). The processor may maintain the date, elapsed heating time and/or occurrence time of any event or condition (e.g., time when a leak occurs, time instruments inserted within drape container, etc.). The processor may measure the elapsed time or record an occurrence time for any desired condition. The processor may maintain the time information internally or utilize any desired external circuitry (e.g., a timer, etc.).

The processor may collect any desired information (e.g., start date and time of solution and/or instrument heating, the time interval the solution and/or instrument was heated, the temperature the solution and/or instrument attained during heating, partial or complete history of time and solution and/or instrument temperature measured at any desired time intervals, facility name and location, patient information, doctor information, type of procedure, type of solution and/or instruments being heated, amount of solution being heated, etc.) from any desired sources (e.g., detection circuitry, temperature controller, user, memory device, another computer or device, etc.).

The reports may be arranged in any fashion and include any desired information. The report information may be arranged and/or presented (e.g., printed, displayed, etc.) in any desired formats (e.g., text, charts, graphs, etc.). The report and/or information may alternatively be stored in a local or remote database or memory device (e.g., local memory, removable memory, etc.) for later retrieval. The reports may include a pre-arranged format or may be programmable or selected by a user via processor input devices. The stand, controller and processor displays may be of any quantity, shape or size, may be disposed at any location on or remote from the stand, may be implemented by any conventional or other displays (e.g., LED, LCD, etc.) and may display any desired information. The information displayed may be selected via controller or processor input devices, or the display may include display controls (e.g., buttons, keys, etc.).

The printer may be implemented by any conventional or other printing device, may be local or remote, may serve any quantity of stands or other devices, and may produce reports on any desired medium (e.g., paper, labels, etc.). The reports may be printed at any specific time or in response to user entered information (e.g., a print command or key). The printer slot may be of any quantity, shape or size and may be disposed at any suitable location on the controller housing. The report may be printed at any desired time before, during or after stand use, and may be retrieved from the stand at any desired time or in any desired manner that preserves a sterile field (e.g., after completion of the medical procedure, after discarding the drape, times when a sterile field is not needed or being employed by the stand, etc.). The communications module may be implemented by any conventional or other communications device or module (e.g., modem, etc.) and may download or transfer an electronic form of the report to any desired device (e.g., PDA, computer, another stand, etc.) at any specific time or in response to user entered information (e.g., transmit command or key). The stands may further be networked to enable retrieval of reports and/or information from a station coupled to the network. The printer and communications module may be disposed at any suitable locations on or remote from the stand. Any desired information may be transmitted between the control circuitry components (e.g., temperature controller, detection circuitry, processor, printer, communications module, displays, etc.) via any conventional or other communications medium or protocols (e.g., hardwire, wireless, network, etc.). The processor may implement or be implemented by the temperature controller. The temperature sensor may be coupled to the temperature controller, microprocessor and/or processor either individually or in any combination or fashion.

Software for the controller, microprocessor and processor may be implemented in any desired computer language and could be developed by one of ordinary skill in the computer arts based on the functional descriptions contained herein. The controller, microprocessor and/or processor may alternatively be implemented by any type of hardware and/or other processing circuitry, and may be available pre-programmed for immediate use. The various functions of the controller, microprocessor and/or processor may be distributed in any manner among any quantity of software modules, processors and/or circuitry.

It is to be understood that the terms "top", "bottom", "front", "rear", "side", "height", "length", "width", "upper", "lower" and the like are used herein merely to describe points of reference and do not limit the present invention to any particular orientation or configuration.

The stand is not limited to the applications or configuration described above, but may be utilized to thermally treat any types of medical or non-medical instruments or other objects (e.g., containers, etc.) at any desired locations.

From the foregoing description, it will be appreciated that the invention makes available a novel heated medical instrument stand with surgical drape and method of detecting fluid and leaks in the stand tray, wherein a medical instrument stand includes a thermally treated tray to thermally treat solution and medical instruments and employs a surgical drape forming a drape container in the tray and including a sensing device to provide signals indicating drape container conditions to the system to facilitate control of system operation.

Having described preferred embodiments of a new and improved heated medical instrument stand with surgical drape and method of detecting fluid and leaks in the stand tray, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A system for thermally treating medical instruments to a desired temperature comprising:

a stand including a base and a support member attached to and extending from said base;

a tray supported by said support member to receive at least one medical instrument;

a drape, covering and substantially conforming to said tray, to form a drape container within said tray to receive a sterile liquid and said at least one medical instrument;

a thermal treatment unit to thermally treat said tray;

a temperature sensor to measure temperature of at least one of said thermal treatment unit, said tray and said liquid; and a controller to control thermal treatment of said tray by said thermal treatment unit in accordance with said measured temperature to thermally treat said liquid and said at least one medical instrument to a desired temperature;

a processor to collect information relating to at least one of said liquid and said at least one medical instrument and to generate a report including said collected information; and a printer to print a hardcopy of said report.

2. The system of claim 1, wherein said stand includes a Mayo stand.

3. The system of claim 1, wherein said drape includes a sensing device to detect and facilitate indication of conditions within said drape container, and wherein said system further includes a detection unit in communication with said sensing device to determine occurrence of said drape container conditions and to control said controller to operate said thermal treatment unit in accordance with said determined drape container conditions.

4. The system of claim 3, wherein said sensing device includes a plurality of conductors each disposed on a sterile drape surface within said drape container and extending therefrom to a non-sterile drape surface, wherein potentials of said conductors are responsive to contact between said conductors and said liquid and indicate conditions of said drape container, and wherein said detection unit determines occurrence of said drape container conditions from said potentials of said conductors.

5. The system of claim 4, wherein said plurality of conductors includes a plurality of electrodes.

6. The system of claim 4, wherein said drape includes an opening defined therein to permit passage of said plurality of conductors therethrough and a material segment attached to a drape surface coincident said opening to seal said opening and secure said plurality of conductors within said drape container.

7. The system of claim 4, wherein said drape includes an opening defined therein to permit passage of said plurality of conductors therethrough and a plurality of material segments, wherein each of the sterile and non-sterile drape surfaces includes at least one of said material segments disposed coincident said opening to seal said opening and secure said plurality of conductors within said drape container.

8. The system of claim 3, wherein said sensing device includes a plurality of conductive and insulating drape segments with potentials of said conductive segments being responsive to contact between said conductive segments and said liquid to indicate conditions of said drape container, and wherein said detection unit determines occurrence of said drape container conditions from said potentials of said conductive segments.

9. The system of claim 3 further including a plurality of indicators to indicate drape container conditions, wherein said indicators are actuable in response to control signals generated by said detection unit in accordance with said determined occurrence of said drape container conditions.

10. The system of claim 9, wherein at least one indicator includes a visual indicator to visually indicate occurrence of a drape container condition.

11. The system of claim 9, wherein at least one indicator includes an audio indicator to produce audio signals to indicate occurrence of a drape container condition.

12. The system of claim 3, wherein said detection unit disables said thermal treatment unit in response to determining the presence of a leak or absence of said liquid within said drape container.

13. The system of claim 3, wherein said detection unit enables said thermal treatment unit in response to determining the presence of said liquid and absence of a leak within said drape container.

14. The system of claim 1, wherein said thermal treatment unit is operative to cool said liquid and said at least one medical instrument in said drape container.

15. The system of claim 1, wherein said thermal treatment unit is operative to heat said liquid and said at least one medical instrument in said drape container.

16. The system of claim 1, wherein said drape includes a pre-formed container portion to form said drape container within said tray.

17. The system of claim 1, wherein at least said controller is disposed within a housing secured to said support member and said drape includes a pre-formed portion configured for placement over said housing.

18. The system of claim 4, wherein said plurality of conductors are each disposed through said drape to extend between said sterile and non-sterile drape surfaces.

19. The system of claim 4, wherein said plurality of conductors each extend along said sterile drape surface and traverse a drape peripheral edge to extend between said sterile and non-sterile drape surfaces.

20. The system of claim 3, wherein said sensing device detects and facilitates indication of conditions of said drape container including the presence of said liquid and a leak within said drape container.

21. A system for thermally treating medical instruments to a desired temperature comprising:
a stand including a base and a support member attached to and extending from said base;
a tray supported by said support member to receive at least one medical instrument;
a drape, covering and substantially conforming to said tray, to form a drape container within said tray to receive a sterile liquid and said at least one medical instrument;
a thermal treatment unit to thermally treat said tray;
a temperature sensor to measure temperature of at least one of said thermal treatment unit, said tray and said liquid;
a controller to control thermal treatment of said tray by said thermal treatment unit in accordance with said measured temperature to thermally treat said liquid and said at least one medical instrument to a desired temperature;
a processor to collect information relating to at least one of said liquid and said at least one medical instrument and to generate a report including said collected information; and
a communications module to establish communications and transfer information with another device.

22. The system of claim 21, wherein said processor generates said report in electronic form and said communications module transmits said report to said other device.

23. The system of claim 21, wherein said stand includes a Mayo stand.

24. The system of claim 21, wherein said drape includes a sensing device to detect and facilitate indication of conditions within said drape container, and wherein said system further includes a detection unit in communication with said sensing device to determine occurrence of said drape container conditions and to control said controller to operate said thermal treatment unit in accordance with said determined drape container conditions.

25. The system of claim 24, wherein said sensing device includes a plurality of conductors each disposed on a sterile drape surface within said drape container and extending therefrom to a non-sterile drape surface, wherein potentials of said conductors are responsive to contact between said conductors and said liquid and indicate conditions of said drape container, and wherein said detection unit determines occurrence of said drape container conditions from said potentials of said conductors.

26. The system of claim 25, wherein said plurality of conductors includes a plurality of electrodes.

27. The system of claim 25, wherein said drape includes an opening defined therein to permit passage of said plurality of conductors therethrough and a material segment attached to a drape surface coincident said opening to seal said opening and secure said plurality of conductors within said drape container.

28. The system of claim 25, wherein said drape includes an opening defined therein to permit passage of said plurality of conductors therethrough and a plurality of material segments, wherein each of the sterile and non-sterile drape surfaces includes at least one of said material segments disposed coincident said opening to seal said opening and secure said plurality of conductors within said drape container.

29. The system of claim 24, wherein said sensing device includes a plurality of conductive and insulating drape segments with potentials of said conductive segments being responsive to contact between said conductive segments and said liquid to indicate conditions of said drape container, and wherein said detection unit determines occurrence of said drape container conditions from said potentials of said conductive segments.

30. The system of claim 24 further including a plurality of indicators to indicate drape container conditions, wherein said indicators are actuable in response to control signals generated by said detection unit in accordance with said determined occurrence of said drape container conditions.

31. The system of claim 30, wherein at least one indicator includes a visual indicator to visually indicate occurrence of a drape container condition.

32. The system of claim 30, wherein at least one indicator includes an audio indicator to produce audio signals to indicate occurrence of a drape container condition.

33. The system of claim 24, wherein said detection unit disables said thermal treatment unit in response to determining the presence of a leak or absence of said liquid within said drape container.

34. The system of claim 24, wherein said detection unit enables said thermal treatment unit in response to determining the presence of said liquid and absence of a leak within said drape container.

35. The system of claim 21, wherein said thermal treatment unit is operative to cool said liquid and said at least one medical instrument in said drape container.

36. The system of claim 21, wherein said thermal treatment unit is operative to heat said liquid and said at least one medical instrument in said drape container.

37. The system of claim 21, wherein said drape includes a pre-formed container portion to form said drape container within said tray.

38. The system of claim 21, wherein at least said controller is disposed within a housing secured to said support member and said drape includes a pre-formed portion configured for placement over said housing.

39. The system of claim 25, wherein said plurality of conductors are each disposed through said drape to extend between said sterile and non-sterile drape surfaces.

40. The system of claim 25, wherein said plurality of conductors each extend along said sterile drape surface and traverse a drape peripheral edge to extend between said sterile and non-sterile drape surfaces.

41. The system of claim 24, wherein said sensing device detects and facilitates indication of conditions of said drape container including the presence of said liquid and a leak within said drape container.

42. A method of thermally treating medical instruments to a desired temperature within a medical instrument thermal treatment system including a stand with a thermally treated tray to receive at least one medical instrument, said method comprising:
(a) disposing a drape over said stand substantially conforming to said tray to form a drape container within said tray;
(b) receiving a sterile liquid and at least one medical instrument within said drape container;
(c) thermally treating said tray, via a thermal treatment unit, and measuring temperature of at least one of said thermal treatment unit, said tray and said liquid; and
(d) controlling thermal treatment of said tray by said thermal treatment unit in accordance with said measured temperature to thermally treat said liquid and said at least one medical instrument to a desired temperature;
(e) collecting information relating to at least one of said liquid and said at least one medical instrument and generating a report including said collected information; and
(f) printing a hardcopy of said report.

43. The method of claim 42, wherein said stand includes a Mayo stand.

44. The method of claim 42, wherein said drape includes a sensing device, and step (c) further includes:
(c.1) detecting conditions within said drape container, via said sensing device, and facilitating indication of said detected drape container conditions; and
step (d) further includes:
(d.1) determining occurrence of said drape container conditions and controlling operation of said thermal treatment unit in accordance with said determined drape container conditions.

45. The method of claim 44, wherein said sensing device includes a plurality of conductors each disposed on a sterile drape surface within said drape container and extending therefrom to a non-sterile drape surface, and step (c.1) further includes:
(c.1.1) altering potentials of said conductors in response to contact between said conductors and said liquid to indicate conditions of said drape container; and
step (d.1) further includes:
(d.1.1) determining occurrence of said drape container conditions from said potentials of said conductors.

46. The method of claim 44, wherein said sensing device includes a plurality of conductive and insulating drape segments, and step (c.1) further includes:
(c.1.1) altering potentials of said conductive segments in response to contact between said conductive segments and said liquid to indicate conditions of said drape container; and
step (d.1) further includes:
(d.1.1) determining occurrence of said drape container conditions from said potentials of said conductive segments.

47. The method of claim 44, wherein step (d) further includes:
(d.2) actuating at least one of a visual and an audio indicator to indicate said determined occurrence of said drape container conditions.

48. The method of claim 44, wherein step (d.1) further includes:
(d.1.1) disabling said thermal treatment unit in response to determining the presence of a leak or absence of said liquid within said drape container.

49. The method of claim 44, wherein step (d.1) further includes:
(d.1.1) enabling said thermal treatment unit in response to determining the presence of said liquid and absence of a leak within said drape container.

50. The method of claim 44, wherein step (c.1) further includes:
(c.1.1) detecting and facilitating indication of said drape container conditions including the presence of said liquid and a leak within said drape container.

51. A method of thermally treating medical instruments to a desired temperature within a medical instrument thermal treatment system including a stand with a thermally treated tray to receive at least one medical instrument, said method comprising:
(a) disposing a drape over said stand substantially conforming to said tray to form a drape container within said tray;
(b) receiving a sterile liquid and at least one medical instrument within said drape container;
(c) thermally treating said tray, via a thermal treatment unit, and measuring temperature of at least one of said thermal treatment unit, said tray and said liquid;
(d) controlling thermal treatment of said tray by said thermal treatment unit in accordance with said measured temperature to thermally treat said liquid and said at least one medical instrument to a desired temperature;
(e) collecting information relating to at least one of said liquid and said at least one medical instrument and generating a report including said collected information; and
(f) establishing communications and transferring information with another device.

52. The method of claim 51, wherein step (f) further includes:
(f.1) generating said report in electronic form and transmitting said report to said other device.

53. The method of claim 51, wherein said stand includes a Mayo stand.

54. The method of claim 51, wherein said drape includes a sensing device, and step (c) further includes:
(c.1) detecting conditions within said drape container, via said sensing device, and facilitating indication of said detected drape container conditions; and
step (d) further includes:
(d.1) determining occurrence of said drape container conditions and controlling operation of said thermal treatment unit in accordance with said determined drape container conditions.

55. The method of claim 54, wherein said sensing device includes a plurality of conductors each disposed on a sterile drape surface within said drape container and extending therefrom to a non-sterile drape surface, and step (c.1) further includes:

(c.1.1) altering potentials of said conductors in response to contact between said conductors and said liquid to indicate conditions of said drape container; and step (d.1) further includes:

(d.1.1) determining occurrence of said drape container conditions from said potentials of said conductors.

56. The method of claim 54, wherein said sensing device includes a plurality of conductive and insulating drape segments, and step (c.1) further includes:

(c.1.1) altering potentials of said conductive segments in response to contact between said conductive segments and said liquid to indicate conditions of said drape container; and step (d.1) further includes:

(d.1.1) determining occurrence of said drape container conditions from said potentials of said conductive segments.

57. The method of claim 54, wherein step (d) further includes:

(d.2) actuating at least one of a visual and an audio indicator to indicate said determined occurrence of said drape container conditions.

58. The method of claim 54, wherein step (d.1) further includes:

(d.1.1) disabling said thermal treatment unit in response to determining the presence of a leak or absence of said liquid within said drape container.

59. The method of claim 54, wherein step (d.1) further includes:

(d.1.1) enabling said thermal treatment unit in response to determining the presence of said liquid and absence of a leak within said drape container.

60. The method of claim 54, wherein step (c.1) further includes:

(c.1.1) detecting and facilitating indication of said drape container conditions including the presence of said liquid and a leak within said drape container.

\* \* \* \* \*